United States Patent
Pluznick et al.

(10) Patent No.: US 10,435,456 B2
(45) Date of Patent: *Oct. 8, 2019

(54) COMPOSITIONS AND METHODS FOR INCREASING THE EXPRESSION AND SIGNALLING OF PROTEINS ON CELL SURFACES

(71) Applicant: THE JOHNS HOPKINS UNIVERSITY, Baltimore, MD (US)

(72) Inventors: Jennifer Pluznick, Lutherville-Timonium, MD (US); Blythe Shepard, Baltimore, MD (US); Niranjana Natarajan, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 247 days.

This patent is subject to a terminal disclaimer.

(21) Appl. No.: 15/115,459

(22) PCT Filed: Jan. 29, 2015

(86) PCT No.: PCT/US2015/013437
§ 371 (c)(1),
(2) Date: Jul. 29, 2016

(87) PCT Pub. No.: WO2015/116771
PCT Pub. Date: Aug. 6, 2016

(65) Prior Publication Data
US 2017/0183392 A1    Jun. 29, 2017

Related U.S. Application Data

(60) Provisional application No. 61/933,022, filed on Jan. 29, 2014.

(51) Int. Cl.
| | | |
|---|---|---|
| C07K 14/72 | (2006.01) | |
| C07K 14/705 | (2006.01) | |
| C07K 14/47 | (2006.01) | |
| C07K 7/06 | (2006.01) | |
| C07K 7/08 | (2006.01) | |

(52) U.S. Cl.
CPC ............. *C07K 14/723* (2013.01); *C07K 7/06* (2013.01); *C07K 7/08* (2013.01); *C07K 14/47* (2013.01); *C07K 14/4705* (2013.01); *C07K 14/705* (2013.01); *C07K 2319/035* (2013.01); *C07K 2319/42* (2013.01)

(58) Field of Classification Search
None
See application file for complete search history.

(56) References Cited

U.S. PATENT DOCUMENTS

| | | | |
|---|---|---|---|
| 5,993,778 A | 11/1999 | Firestein et al. | |
| 7,138,242 B2 | 11/2006 | Reed et al. | |
| 7,691,592 B2 | 4/2010 | Matsunami et al. | |
| 7,745,391 B2 | 6/2010 | Mintz et al. | |
| 9,783,585 B2* | 10/2017 | Pluznick | C07K 14/705 |
| 2006/0057640 A1 | 3/2006 | Matsunami et al. | |
| 2008/0279834 A1* | 11/2008 | Garaczi | A61K 49/0004 |
| | | | 424/93.71 |
| 2008/0305547 A1 | 12/2008 | Malnic | |
| 2009/0092997 A1 | 4/2009 | Matsunami et al. | |
| 2009/0136968 A1 | 5/2009 | Sallman | |
| 2009/0155267 A1 | 6/2009 | Priest et al. | |

OTHER PUBLICATIONS

Hague, C., et al. (2004) "Olfactory receptor surface expression is driven by association with B2-Adrenergic receptor", PNAS, vol. 101, No. 37, pp. 13672-13676.
Matsunami, H. (2005) "Functional expression of mammalian odorant receptors", Chemical Senses, vol. 30, suppl 1, i95-i96.
Neuhaus, E., et al. (2006) "A specific heat shock protein enhances the expression of mammalian olfactory receptor proteins", Chemical Senses, vol. 31, pp. 445-452.
Shepard, B., et al. (2013) "A cleavable N-terminal signal peptide promotes widespread olfactory receptor surface expression in HEK293T cells", PLOS ONE, vol. 8, No. 7, e68758.
Wu, L., et al. (2012) "Receptor-transporting protein 1 short (RTP1S) mediates translocation and activation of odorant receptors by acting through multiple steps", The Journal of Biological Chemistry, vol. 287, No. 26, pp. 22287-22294.
Wellerdieck, C., et al. "Functional expression of odorant receptors of the zebrafish Danio rerio and of the nematode C. elegans in HEK293 cells", Chem. Senses (1997) 22, 467-476.
Malnic, B., "Searching for the Ligands of Odorant Receptors", Mol Neurobiol (2007) 35, 175-181.

(Continued)

*Primary Examiner* — Addison D Ault
(74) *Attorney, Agent, or Firm* — Johns Hopkins Technology Ventures

(57) ABSTRACT

The present invention relates to the field of protein expression. More specifically, the present invention provides compositions and methods for increasing the expression and signaling of proteins on cell surfaces. In particular embodiments, the present invention provides nucleic acids and amino acid sequences useful for improving/increasing protein expression on the cell surface. In several embodiments, the sequences are operably linked to the N-terminal end of the protein of interest. The nucleic acid sequence encoding the sequence tag and the protein can comprise part of an expression vector. The protein can be expressed with the N-terminal sequence tag. In certain embodiments, the sequences of the present invention can be used with one or more chaperone or accessory proteins. In particular embodiments, the one or more chaperone/accessory proteins are encoded by the same vector or separate vectors. In other embodiments, the chaperone/accessory proteins are encoded the same vector that encodes the protein of interest.

21 Claims, 17 Drawing Sheets

Specification includes a Sequence Listing.

(56) References Cited

OTHER PUBLICATIONS

Hamana, H., "Heterologous functional expression system for odorant receptors", J Neurosci. Met., (2010) 185, Issue 2, 213-220.
Chan, D., et al., "Signal peptide cleavage is essential for surface expression of a regulatory T cell surface protein, leucine rich repeat containing 32 (LRRC32)", (2011) BMC Biochem 12: 27 (2011).
Dunham, J., et al., "Enhancement of the surface expression of G protein-coupled receptors" Trends Biotechnol (2009) 27: 541-545.
Katada, S., et al., "Odorant response assays for a heterologously expressed olfactory receptor", Biochem Biophys Res Commun (2003) 305: 964-969.
Zhuang, H., et al., "Evaluating cell-surface expression and measuring activation of mammalian odorant receptors in heterologous cells", Nat Protoc (2008) 3: 1402-1413.
Pluznick, J., et al., "Functional expression of the olfactory signaling system in the kidney" Proc Natl Acad Sci USA (2009) 106: 2059-2064.
Touhara, K., "Deorphanizing vertebrate olfactory receptors: recent advances in odorant-response assays" Neurochem Int (2007) 51: 132-139.
Wetzel, C., et al., "Specificity and sensitivity of a human olfactory receptor functionally expressed in human embryonic kidney 293 cells and Xenopus Laevis oocytes", J Neurosci (1999) 19: 7426-7433.
Lu, M., et al., "Endoplasmic reticulum retention, degradation, and aggregation of olfactory G-protein coupled -receptors" Traffic (2003) 4:416-433.
McClintock, T., et al., "Trafficking prerogatives of olfactory receptors" Neuroreport (2003) 14: 1547-1552.
Bush, C., et al., "Olfactory receptor trafficking to the plasma membrane" Cell Mol Life Sci (2008) 65: 2289-2295.
Krautwurst, D., et al., "Identification of ligands for olfactory receptors by functional expression of a receptor library", Cell (1998) 95: 917-926.
Matsunami, H., et al., "Trafficking of mammalian chemosensory receptors by receptor-transporting proteins" Ann N Y Acad Sci (2009) 1170: 153-156.
Zhuang, H., et al, "Synergism of accessory factors in functional expression of mammalian odorant receptors" J Biol Chem (2007) 282: 15284-15293.
Wu, L., et al., "Receptor transporting protein 1 short (RTP1S) mediates translocation and activation of odorant receptors by acting through multiple steps" J Biol Chem (2012) 287: 22287-22294.
Vondannecker, L., et al., "Ric-8B promotes functional expression of odorant receptors" Proc Natl Acad Sci USA (2006)103: 9310-9314.
Schulein, R., et al., "Functional significance of cleavable signal peptides of G protein-coupled receptors" Eur J Cell Biol (2012) 91: 294-299.
Saito, H., et al., "RTP family members induce functional expression of mammalian odorant receptors", Cell, Nov. 24, 2004, vol. 119, No. 5, pp. 679-691.
Shepard, et al., "A cleavable n-terminal signal peptide promotes widespread olfactory receptor surface expression in HEK293T cells" PLOS ONE (2013) vol. 8, No. 7, e68758.
UniProtKB/Swiss-Prot Accession No. Q5RF01, created Oct. 11, 2005 and updated Nov. 25, 2008 [online], [retrieved Dec. 14, 2016], retrieved from the Internet: <http://www.signalpeptide.de/index.php?sess=&m=listspdb_mammalia&s=details&id=2537&listname=>, 5 pages.
Godfrey, P., et al., (2004) The mouse olfactory receptor gene family. Proc Natl Acad Sci USA 101: 2156-2161.
Malnic, B., et al., (2004) The human olfactory receptor gene family. Proc Natl Acad Sci USA 101: 2584-2589.
Buck, L., et al., (1991) A novel multigene family may encode odorant receptors: a molecular basis for odor recognition. Cell 65: 175-187.
Mombaerts, P., (2004) Genes and ligands for odorant, vomeronasal and taste receptors. Nat Rev Neurosci 5: 263-278.
Gaillard, I., et al., (2002) A single olfactory receptor specifically binds a set of odorant molecules. Eur J Neurosci 15: 409-418.
Hague, C., et al., (2004) Olfactory receptor surface expression is driven by association with the beta2-adrenergic receptor Proc Natl Acad Sci USA 101: 13672-13676.
Lu, M., et al., (2004) Endoplasmic reticulum degradation impedes olfactory G-protein coupled receptor functional expression. BMC Cell Biol 5: 34.
Hall, R., (2009) Olfactory receptor interactions with other receptors. Ann. N Y Acad Sci 1170: 147-149.
Hansson, M., et al., (2008) PCR-mediated deletion of plasmid DNA. Anal Biochem 375: 373-375.
Belluscio, L., et al., (1998) Mice deficient in G(olf) are anosmic. Neuron 20: 69-81.
Kajiya, K., et al., (2001) Molecular bases of odor discrimination: Reconstitution of olfactory receptors that recognize overlapping sets of odorants. J Neurosci 21: 6018-6025.
Nara, K., et al., (2011) A large-scale analysis of odor coding in the olfactory epithelium. J Neurosci 31: 9179-9191.
Saito, H., et al., (2009) Odor coding by a Mammalian receptor repertoire. Sci Signal 2: ra9.
Zimmermann, R., et al., (2011) Protein translocation across the ER membrane. Biochim Biophys Acta 1808: 912-924.
Zampatis, D., et al., (2012) The protease-activated receptor 1 possesses a functional and cleavable signal peptide which is necessary for receptor expression. FEBS Lett 586: 2351-2359.
Bryksin, A., et al., (2010) Overlap extension PCR cloning: a simple and reliable way to create recombinant plasmids. BioTechniques 48: 463-465.
Guan, X., et al., (1992) Enhancement of membrane insertion and function in a type IIIb membrane protein following introduction of a cleavable signal peptide. J Biol Chem 267: 21995-21998.

\* cited by examiner

LF691 + RTP + Ric8b
surface            total            nucleus
 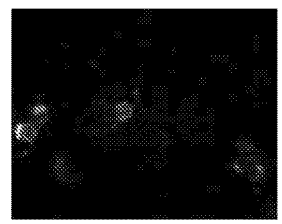 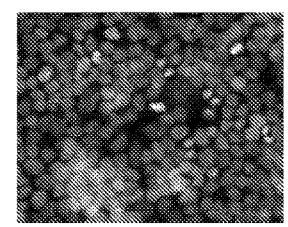
 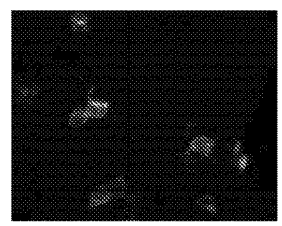 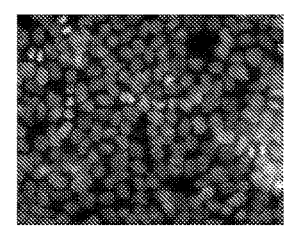
FIG. 4

NUCLEOTIDE

<u>ATG AGA CCC CAG ATC CTG CTG CTC CTG GCC CTG CTG ACC CTA GGC CTG GCT</u> *TAC CCA TAC GAT GTT CCA GAT TAC GCT*ATC GAA TTG *<u>ATG AAC GGG ACC GAG GGC CCA AAC TTC TAC GTG CCT TTC TCC AAC AAG ACG GGC GTG GTG</u>* <u>GAA TTC</u> (SEQ ID NO:11)

Regular Font/Underlined:    Lucy tag
Italics:    HA tag
Bold:    9 nucleotide linker
Italics/Underlined:    Rho tag
Bold/Underlined:    EcoRI site for cloning

AMINO ACID

MRPQILLLLALLTLGLA*YPYDVPDYA*IEL*<u>MNGTEGPNFYVPFSNKTGVV</u>*EF (SEQ ID NO:12)

Regular Font/Underlined:    Lucy tag
Italics:    HA tag
Bold:    9 nucleotide linker
Italics/Underlined:    Rho tag
Bold/Underlined:    EcoRI site for cloning

FIG. 7

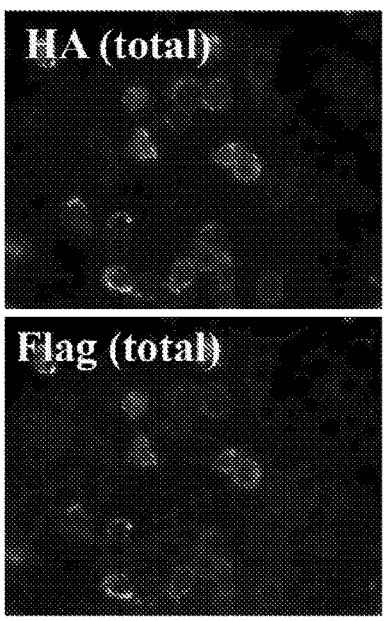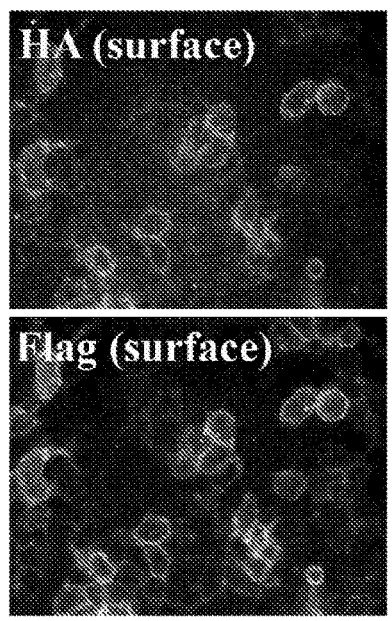
FIG. 10A and 10B
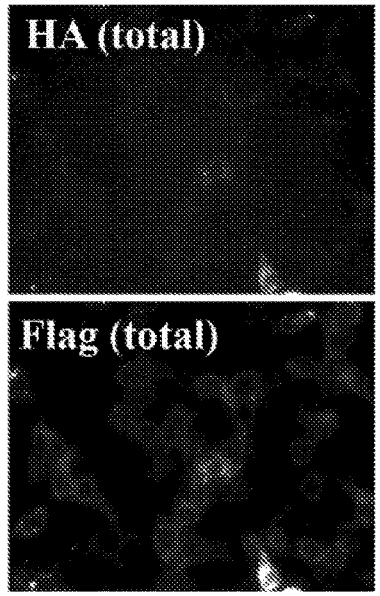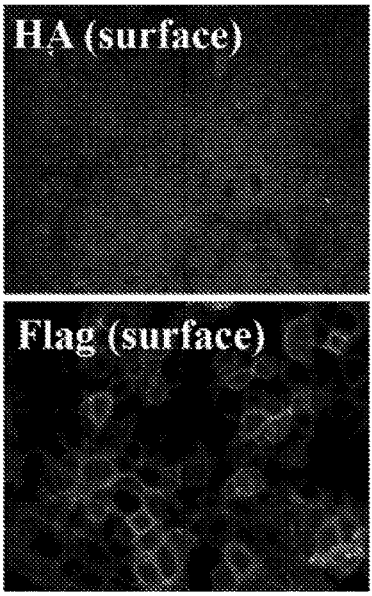
FIG. 10C and 10D

NUCLEOTIDE

<u>ATG AGA CCC CAG ATC CTG CTG CTC CTG GCC CTG CTG ACC CTA GGC CTG GCT</u> *GAT TAC AAG GAC GAC GAC GAT AAG* ATC GAA TTG *ATG AAC GGG ACC GAG GGC CCA AAC TTC TAC GTG CCT TTC TCC AAC AAG ACG GGC GTG GTG* GAA TTC
(SEQ ID NO:17)

| Regular Font/Underlined: | Lucy tag |
| Italics: | Flag tag |
| Bold: | 9 nucleotide linker |
| Italics/Underlined: | Rho tag |
| Bold/Underlined: | EcoRI site for cloning |

AMINO ACID

<u>MRPQILLLLALLTLGLA</u>*DYKDDDDK*IEL*MNGTEGPNFYVPFSNKTGVV*EF
(SEQ ID NO:18)

| Regular Font/Underlined: | Lucy tag |
| Italics: | Flag tag |
| Bold: | Linker |
| Italics/Underlined: | Rho tag |
| Bold/Underlined: | EcoRI site for cloning |

FIG. 16

SEQUENCE LISTING

<160> NUMBER OF SEQ ID NOS: 18

<210> SEQ ID NO 1
<211> LENGTH: 147
<212> TYPE: DNA
<213> ORGANISM: Artificial Sequence
<220> FEATURE:
<223> OTHER INFORMATION: Nucleotide sequence comprising Lucy tag, HA tag, linker and Rho tag

<400> SEQUENCE: 1
atgagacccc agatcctgct gctcctggcc ctgctgaccc taggcctggc ttacccatac    60
gatgttccag attacgctat cgaattgatg aacgggaccg agggcccaaa cttctacgtg     120
cctttctcca acaagacggg cgtggtg                                         147

<210> SEQ ID NO 2
<211> LENGTH: 49
<212> TYPE: PRT
<213> ORGANISM: Artificial Sequence
<220> FEATURE:
<223> OTHER INFORMATION: Amino acid sequence comprising Lucy tag, HA
      tag, linker and Rho tag

<400> SEQUENCE: 2

Met Arg Pro Gln Ile Leu Leu Leu Leu Ala Leu Leu Thr Leu Gly Leu
1               5                   10                  15

Ala Tyr Pro Tyr Asp Val Pro Asp Tyr Ala Ile Glu Leu Met Asn Gly
            20                  25                  30

Thr Glu Gly Pro Asn Phe Tyr Val Pro Phe Ser Asn Lys Thr Gly Val
        35                  40                  45

Val

<210> SEQ ID NO 3
<211> LENGTH: 17
<212> TYPE: PRT
<213> ORGANISM: Artificial Sequence
<220> FEATURE:
<223> OTHER INFORMATION: Amino acid sequence of Lucy tag

<400> SEQUENCE: 3

Met Arg Pro Gln Ile Leu Leu Leu Leu Ala Leu Leu Thr Leu Gly Leu
1               5                   10                  15

Ala

<210> SEQ ID NO 4
<211> LENGTH: 51
<212> TYPE: DNA
<213> ORGANISM: Artificial Sequence
<220> FEATURE:
<223> OTHER INFORMATION: Nucleotide sequence of the Lucy tag

<400> SEQUENCE: 4
atgagacccc agatcctgct gctcctggcc ctgctgaccc taggcctggc t              51

<210> SEQ ID NO 5
<211> LENGTH: 27
<212> TYPE: DNA
<213> ORGANISM: Artificial Sequence
<220> FEATURE:
<223> OTHER INFORMATION: Nucleotide sequence of the HA tag

<400> SEQUENCE: 5
tacccatacg atgttccaga ttacgct                                         27

<210> SEQ ID NO 6
<211> LENGTH: 9
<212> TYPE: PRT
<213> ORGANISM: Artificial Sequence
<220> FEATURE:
<223> OTHER INFORMATION: Amino acid sequence of the HA tag

<400> SEQUENCE: 6

Tyr Pro Tyr Asp Val Pro Asp Tyr Ala
1               5

<210> SEQ ID NO 7
<211> LENGTH: 9
<212> TYPE: DNA
<213> ORGANISM: Artificial Sequence
<220> FEATURE:
<223> OTHER INFORMATION: 9 nucleotide linker

<400> SEQUENCE: 7 atcgaattg                                                                                    9

<210> SEQ ID NO 8
<211> LENGTH: 3
<212> TYPE: PRT
<213> ORGANISM: Artificial Sequence
<220> FEATURE:
<223> OTHER INFORMATION: 3 amino acid linker

<400> SEQUENCE: 8

Ile Glu Leu
1

<210> SEQ ID NO 9
<211> LENGTH: 60
<212> TYPE: DNA
<213> ORGANISM: Artificial Sequence
<220> FEATURE:
<223> OTHER INFORMATION: Nucleotide sequence of the Rho tag

<400> SEQUENCE: 9
atgaacggga ccgagggccc aaacttctac gtgcctttct ccaacaagac gggcgtggtg      60

<210> SEQ ID NO 10
<211> LENGTH: 20
<212> TYPE: PRT
<213> ORGANISM: Artificial Sequence
<220> FEATURE:
<223> OTHER INFORMATION: Amino acid sequence of the Rho tag

<400> SEQUENCE: 10

Met Asn Gly Thr Glu Gly Pro Asn Phe Tyr Val Pro Phe Ser Asn Lys
1               5                   10                  15

Thr Gly Val Val
            20

<210> SEQ ID NO 11
<211> LENGTH: 153
<212> TYPE: DNA
<213> ORGANISM: Artificial Sequence
<220> FEATURE:
<223> OTHER INFORMATION: Nucleotide sequence encoding the Lucy tag, HA
      tag, linker, Rho tag, EcoRI site for cloning

<400> SEQUENCE: 11
atgagacccc agatcctgct gctcctggcc ctgctgaccc taggcctggc ttacccatac      60
gatgttccag attacgctat cgaattgatg aacgggaccg agggcccaaa cttctacgtg     120
cctttctcca acaagacggg cgtggtggaa ttc                                  153

<210> SEQ ID NO 12
<211> LENGTH: 51
<212> TYPE: PRT
<213> ORGANISM: Artificial Sequence
<220> FEATURE:
<223> OTHER INFORMATION: Amino acid sequence of the Lucy tag, HA tag,
      linker, Rho tag, EcoRI site for cloning

<400> SEQUENCE: 12

Met Arg Pro Gln Ile Leu Leu Leu Ala Leu Leu Thr Leu Gly Leu
1               5                   10                  15

Ala Tyr Pro Tyr Asp Val Pro Asp Tyr Ala Ile Glu Leu Met Asn Gly
            20                  25                  30

Thr Glu Gly Pro Asn Phe Tyr Val Pro Phe Ser Asn Lys Thr Gly Val
                35                  40                  45

Val Glu Phe
    50

<210> SEQ ID NO 13
<211> LENGTH: 144
<212> TYPE: DNA
<213> ORGANISM: Artificial Sequence
<220> FEATURE:
<223> OTHER INFORMATION: Nucleotide sequence comprising Lucy tag, flag
      tag, linker and Rho tag

<400> SEQUENCE: 13
atgagacccc agatcctgct gctcctggcc ctgctgaccc taggcctggc tgattacaag      60
gacgacgacg ataagatcga attgatgaac gggaccgagg gcccaaactt ctacgtgcct    120
ttctccaaca agacgggcgt ggtg                                            144

<210> SEQ ID NO 14
<211> LENGTH: 48
<212> TYPE: PRT
<213> ORGANISM: Artificial Sequence
<220> FEATURE:
<223> OTHER INFORMATION: Amino acid sequence comprising Lucy tag, flag
      tag, linker and Rho tag

<400> SEQUENCE: 14

Met Arg Pro Gln Ile Leu Leu Leu Ala Leu Leu Thr Leu Gly Leu
1               5                   10                  15

Ala Asp Tyr Lys Asp Asp Asp Lys Ile Glu Leu Met Asn Gly Thr
            20                  25                  30

Glu Gly Pro Asn Phe Tyr Val Pro Phe Ser Asn Lys Thr Gly Val Val
        35                  40                  45

<210> SEQ ID NO 15
<211> LENGTH: 24
<212> TYPE: DNA
<213> ORGANISM: Artificial Sequence
<220> FEATURE:
<223> OTHER INFORMATION: Nucleotide sequence of the Flag tag

<400> SEQUENCE: 15
gattacaagg acgacgacga taag                                             24

<210> SEQ ID NO 16
<211> LENGTH: 8
<212> TYPE: PRT
<213> ORGANISM: Artificial Sequence
<220> FEATURE:
<223> OTHER INFORMATION: Amino acid sequence of the Flag tag

<400> SEQUENCE: 16

Asp Tyr Lys Asp Asp Asp Asp Lys
1               5

<210> SEQ ID NO 17
<211> LENGTH: 150

```
<212> TYPE: DNA
<213> ORGANISM: Artificial Sequence
<220> FEATURE:
<223> OTHER INFORMATION: Nucleotide sequence encoding the Lucy tag, Flag
      tag, linker, Rho tag, EcoRI site for cloning

<400> SEQUENCE: 17
atgagacccc agatcctgct gctcctggcc ctgctgaccc taggcctggc tgattacaag      60
gacgacgacg ataagatcga attgatgaac gggaccgagg gcccaaactt ctacgtgcct    120
ttctccaaca agacgggcgt ggtggaattc                                      150

<210> SEQ ID NO 18
<211> LENGTH: 50
<212> TYPE: PRT
<213> ORGANISM: Artificial Sequence
<220> FEATURE:
<223> OTHER INFORMATION: Amino acid sequence of the Lucy tag, Flag tag,
      linker, Rho tag and EcoRI cloning site

<400> SEQUENCE: 18

Met Arg Pro Gln Ile Leu Leu Leu Leu Ala Leu Leu Thr Leu Gly Leu
1               5                   10                  15

Ala Asp Tyr Lys Asp Asp Asp Lys Ile Glu Leu Met Asn Gly Thr
            20                  25                  30

Glu Gly Pro Asn Phe Tyr Val Pro Phe Ser Asn Lys Thr Gly Val Val
        35                  40                  45

Glu Phe
    50
```

COMPOSITIONS AND METHODS FOR INCREASING THE EXPRESSION AND SIGNALLING OF PROTEINS ON CELL SURFACES

CROSS-REFERENCE TO RELATED APPLICATIONS

This application is a 35 U.S.C. § 371 U.S. national entry of International Application PCT/US2015/013437, having an international filing date of Jan. 29, 2015, which claims the benefit of U.S. Provisional Application No. 61/933,022, filed Jan. 29, 2014, the content of each of the aforementioned applications is herein incorporated by reference in their entirety.

STATEMENT OF GOVERNMENTAL INTEREST

This invention was made with government support under grant no. R00DK081610 and grant no. F32-DK096780, awarded by the National Institutes of Health. The government has certain rights in the invention.

FIELD OF THE INVENTION

The present invention relates to the field of protein expression. More specifically, the present invention provides compositions and methods for increasing the expression and signaling of proteins on cell surfaces.

INCORPORATION-BY-REFERENCE OF MATERIAL SUBMITTED ELECTRONICALLY

This application contains a sequence listing. It has been submitted electronically via EFS-Web as an ASCII text file entitled "P12834-02_S25.txt." The sequence listing is 6,563 bytes in size, and was created on Jan. 6, 2015. It is hereby incorporated by reference in its entirety.

BACKGROUND OF THE INVENTION

Olfactory receptors (ORs) are seven transmembrane domain G protein-coupled receptors (GPCRs) that govern the sense of smell in the olfactory epithelium, and comprise the largest gene family in the genome (~1000 OR genes in mice [1] and ~300 [2] in humans). Although this family was first identified over 20 years ago [3], the majority of ORs remain orphan receptors, with no known ligand. This is due, in large part, to the fact that OR deorphanization is typically attempted using in vitro ligand screening assays in heterologous cell systems which require surface expression of the OR as a prerequisite for the assay (i.e., HEK293T cells or *Xenopus* oocytes) [4-7]. Unfortunately, many ORs do not traffic to the cell surface in heterologous cell systems; rather, they are retained in the ER and degraded [8-10], making ligand assignment impossible. To combat this problem, studies have utilized the co-expression of various accessory proteins and/or the addition of N-terminal tags [11-14]. For example, the addition of the first 20 amino acids of rhodopsin onto the N-terminus of ORs (Rho tag) enhances OR surface expression for a number of ORs [15]. Similarly, receptor transporting protein (RTP), originally identified as a potential chaperone for ORs [16,17], also enhances expression of multiple ORs. A recent study showed that the best surface expression was achieved [18] by co-expressing the short form of RTP (RTP1S) [19], Ric8b (a putative GEF) [20] and $G_{\alpha olf}$ (the G protein that couples to ORs in the olfactory epithelium) [21] with Rho-tagged ORs. While these tools have been beneficial to the field [5, 15, 16, 18, 20, 22-24] and are the most reliable enhancers of OR surface expression available to date, their effects are not universal. Despite these developments, many ORs are still unable to reach the cell surface when heterologously expressed, and thus remain as orphan receptors.

As membrane proteins, ORs enter the biosynthetic pathway upon translocation into the endoplasmic reticulum (ER). Typically, this is accomplished co-translationally where a signal peptide serves to mediate ER translocation through the heterotrimeric Sec61 complex that forms a channel in the ER membrane [25]. While most GPCRs use one of their transmembrane domains (TMD) as a signal anchor sequence, a small subset of GPCRs and other TMD proteins (and all secretory proteins) have cleavable signal peptides which are found at the extreme N-terminus of the immature protein [26,27]. As their name implies, these cleavable signal peptides are not incorporated into the mature protein; rather they are cleaved off in the ER membrane upon translocation. While cleavable signal peptides do not have a conserved sequence, they do share characteristic features including a hydrophobic region flanked by polar amino acids [25,26].

Recently, the single-spanning membrane protein, Leucine Rich Repeat Containing 32 (LRRC32) was found to possess a leucine-rich 17-amino acid cleavable signal peptide (MRPQILLLLALLTLGLA) (SEQ ID NO:3) which is required for proper ER translocation and surface expression in both T regulatory cells (where it is natively expressed) as well as in HEK293T cells [28]. Because the addition of other cleavable signal peptides has been shown to enhance surface expression for some GPCRs in cell culture [29,30], we hypothesized that the addition the LRRC32 signal peptide may promote surface expression of ORs. Importantly, as signal peptides are cleaved off in the ER, the addition of such a tag would not affect the mature protein, preventing any potential alteration or interference with ligand binding.

SUMMARY OF THE INVENTION

The present invention is based, at least in part, on the discovery of an N-terminal tag sequence which aids in olfactory receptor trafficking. When expressed exogenously in mammalian cells, olfactory receptors (ORs) fail to traffic to the cell surface. This is a problem in the field as receptor ligands cannot be assayed unless the receptor is present on the cell surface. Either alone or in combination with chaperone proteins, this novel tag allows all ORs assayed thus far to reach the cell surface.

Accordingly, in one aspect, the present invention provides nucleic acids/polynucleotide and amino acid/polypeptide sequences useful for improving/increasing protein expression on the cell surface. In several embodiments, the sequences are operably linked to the N-terminal end of the protein of interest. The nucleic acid sequence encoding the sequence tag and the protein comprise part of an expression vector. The protein is expressed with the N-terminal sequence tag. In certain embodiments, the sequences of the present invention can be used in conjunction with one or more chaperone or accessory proteins. In particular embodiments, the one or more chaperone/accessory proteins are encoded by the same vector or separate vectors. In other embodiments, the chaperone/accessory proteins are encoded the same vector that encodes the protein of interest.

Using the compositions and methods of the present invention, numerous proteins can be expressed on the surface of a host cell. Such proteins can be receptor proteins. In several embodiments, the receptor proteins are olfactory receptors. Olfactory receptors can include, but are not limited to, Olfr78, Olfr51E2, mOREG (Olfr73), Olf145, Olfr691, Olfr52B2, Olfr99, Olfr693, Olfr805, Olfr1392, Olfr1393, Olfr90, Olfr545, Olfr985, and Olfr894. In other embodiments, the receptor proteins are G-protein coupled receptor proteins including, but not limited to, GPR160. Indeed, the compositions and methods of the present invention can be used to express any one of a number of proteins that do not traffic properly and/or do not already have a native signal sequence.

In another embodiment, the present invention provides composition encoding a cleavable signal peptide linked to the N-terminus of a protein of interest, i.e., a cell surface-expressed protein. In a specific embodiment, the cleavable signal peptide comprises the Lucy tag described herein. In a more specific embodiment, the Lucy tag comprises SEQ ID NO:3. In another embodiment, the Lucy tag can further comprise an HA tag. In yet another embodiment, the Lucy tag can further comprise a Rho tag. In certain embodiments, the Lucy tag further comprises an HA tag and a Rho tag. The tags (Lucy, HA, Rho, and/or the like) can be linked (or not) with a linker. Thus, a composition that is linked to the N-terminus of a protein of interest may comprise SEQ ID NO:2, SEQ ID NO:3 or SEQ ID NO:12. Such compositions can be used to express a receptor protein including, G-protein coupled receptors, olfactory receptors, and the like, on the cell surface.

In alternative embodiments, the Lucy tag can further comprise a Flag tag. In yet another embodiment, the Lucy tag can further comprise a Rho tag. In certain embodiments, the Lucy tag further comprises a Flag tag and a Rho tag. The tags (Lucy, Flag, Rho and/or the like) can be linked (or not) with a linker. Thus, a composition that is linked to the N-terminus of a protein of interest may comprise SEQ ID NO:14, SEQ ID NO:3 or SEQ ID NO:18. Such compositions can be used to express a receptor protein including, G-protein coupled receptors, olfactory receptors, and the like, on the cell surface.

Indeed, as described herein, the Lucy-HA tag performs as well as or better than Lucy-Flag, and that the Lucy tag (in addition to aiding surface expression of olfactory receptors, or ORs) also works for an unrelated G-protein coupled receptor, Gpr160. This shows that the Lucy tag can be used to aid in surface trafficking for receptors beyond the OR family.

The protein of interest can be any surface expressed protein. In certain embodiments, the protein of interest is an olfactory receptor. Such a protein can include, but is not limited to, Olfr78, Olfr51E2, mOREG (Olfr73), Olf145, Olfr691, Olfr52B2, Olfr99, Olfr693, Olfr805, Olfr1392, Olfr1393, Olfr90, Olfr545, Olfr985, and Olfr894.

The present invention can be used to increase expression, trafficking, and/or signaling of the protein of interest to the cell surface. In particular embodiments, the present invention can be utilized with olfactory receptor proteins and used in assays by perfume, fragrance, flavor or food companies. The system or assay can further utilize one or more chaperone/accessory proteins to assist in the expression, trafficking, and/or signaling of the protein of interest to the cell surface. Examples of such proteins include, but are not limited to, RTPL1, RTP1S, RTP2, REEP, β-adrenergic receptor, heat shock protein 70, Ric8b, Gαolf and combinations of the foregoing.

BRIEF DESCRIPTION OF THE FIGURES

FIG. 4. Two examples of Lucy-Flag-Rho-691 co-transfected with RTP1s and Ric8b, and stained for surface Flag (unpermeabilized cells), total Flag and with a nuclear stain.

FIG. 7 shows the nucleotide (SEQ ID NO:11) and amino acid (SEQ ID NO:12) sequence of Lucy tag+HAtag+linker+Rho tag+EcoRI site for cloning.

FIG. 10. The Lucy tag is a cleavable signal peptide. HA-Flag-Rho-Olfr691 (A and B) or HA-Lucy-Flag-Rho-Olfr691 (C and D) constructs were expressed in HEK293T cells along with RTP1S. Cells were fixed and stained with both an HA and Flag antibody (A and C) to detect total tagged OR or surface labeled with the HA and Flag antibodies (B and D) to detect surface-associated OR. HA surface stain is observed only in the absence of the Lucy tag, indicating a functional Lucy cleavage site.

FIG. 16 shows the nucleotide (SEQ ID NO:17) and amino acid (SEQ ID NO:18) sequence of Lucy tag+Flag tag+Rho tag.

DETAILED DESCRIPTION OF THE INVENTION

Figure 1:
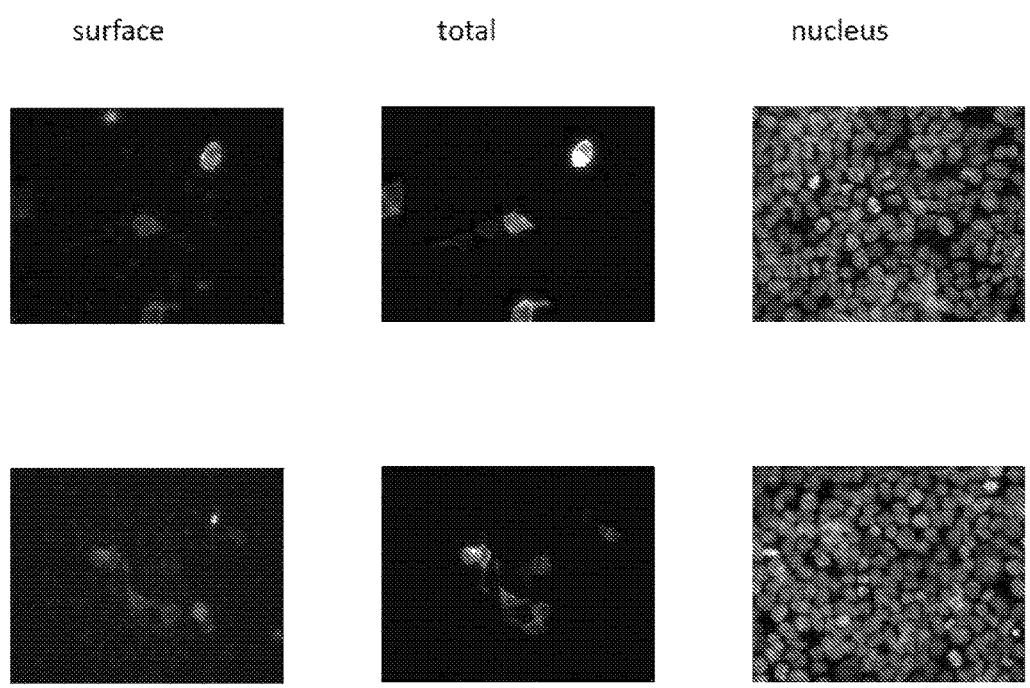
FIG. 1. Two examples of Lucy-HA-Rho-691 stained for surface HA (unpermeabilized cells), total HA and with a nuclear stain.

It is understood that the present invention is not limited to the particular methods and components, etc., described herein, as these may vary. It is also to be understood that the terminology used herein is used for the purpose of describing particular embodiments only, and is not intended to limit the scope of the present invention. It must be noted that as used herein and in the appended claims, the singular forms "a," "an," and "the" include the plural reference unless the context clearly dictates otherwise. Thus, for example, a reference to a "protein" is a reference to one or more proteins, and includes equivalents thereof known to those skilled in the art and so forth.

Unless defined otherwise, all technical and scientific terms used herein have the same meaning as commonly understood by one of ordinary skill in the art to which this invention belongs. Specific methods, devices, and materials are described, although any methods and materials similar or equivalent to those described herein can be used in the practice or testing of the present invention.

All publications cited herein are hereby incorporated by reference including all journal articles, books, manuals, published patent applications, and issued patents. In addition, the meaning of certain terms and phrases employed in the specification, examples, and appended claims are provided. The definitions are not meant to be limiting in nature and serve to provide a clearer understanding of certain aspects of the present invention.

The term "nucleic acid" or "polynucleotide" refers to a polymeric form of nucleotides of any length, either ribonucleotides and/or deoxyribonucleotides. These terms include a single-, double- or triple-stranded DNA, genomic DNA, cDNA, RNA, DNA-RNA hybrid, or a polymer comprising purine and pyrimidine bases, or other natural, chemically, biochemically modified, non-natural or derivatized nucleotide bases. The backbone of the nucleic acid can comprise sugars and phosphate groups (as may typically be found in RNA or DNA), or modified or substituted sugar or phosphate groups. Alternatively, the backbone of the nucleic acid can comprise a polymer of synthetic subunits such as phosphoramidates and thus can be an oligodeoxynucleotide phosphoramidate (P—NH$_2$) or a mixed phosphoramidate-phosphodiester oligomer. In addition, a double-stranded nucleic acid can be obtained from the single stranded nucleic acid product of chemical synthesis either by synthesizing the complementary strand and annealing the strands under appropriate conditions, or by synthesizing the complementary strand de novo using a DNA polymerase with an appropriate primer.

The following are non-limiting examples of nucleic acids: a gene or gene fragment, exons, introns, mRNA, tRNA, rRNA, ribozymes, cDNA, recombinant nucleic acids, branched nucleic acids, plasmids, vectors, isolated DNA of any sequence, isolated RNA of any sequence, nucleic acid probes, and primers. A nucleic acid may comprise modified nucleotides, such as methylated nucleotides and nucleotide analogs, uracyl, other sugars and linking groups such as fluororibose and thioate, and nucleotide branches. The sequence of nucleotides may be interrupted by non-nucleotide components. A nucleic acid may be further modified after polymerization, such as by conjugation with a labeling component. Other types of modifications included in this definition are caps, substitution of one or more of the naturally occurring nucleotides with an analog, and introduction of means for attaching the nucleic acid to proteins, metal ions, labeling components, other nucleic acids, or a solid support.

The terms "isolated," "purified," or "biologically pure" refer to material that is free to varying degrees from components which normally accompany it as found in its native state. Various levels of purity may be applied as needed according to this invention in the different methodologies set forth herein; the customary purity standards known in the art may be used if no standard is otherwise specified.

By "isolated nucleic acid (or polynucleotide) molecule" is meant a nucleic acid (e.g., a DNA, RNA, or analog thereof) that is free of the genes which, in the naturally occurring genome of the organism from which the nucleic acid molecule of the present invention is derived, flank the gene. The term therefore includes, for example, a recombinant DNA that is incorporated into a vector, into an autonomously replicating plasmid or virus; or into the genomic DNA of a prokaryote or eukaryote; or that exists as a separate molecule (for example, a cDNA or a genomic or cDNA fragment produced by PCR or restriction endonuclease digestion) independent of other sequences. In addition, the term includes an RNA molecule which is transcribed from a DNA molecule, as well as a recombinant DNA which is part of a hybrid gene encoding additional polypeptide sequence.

As used herein, the term "operably linked" means that nucleic acid sequences or proteins are operably linked when placed into a functional relationship with another nucleic acid sequence or protein. For example, a promoter sequence is operably linked to a coding sequence if the promoter promotes transcription of the coding sequence. As a further example, a repressor protein and a nucleic acid sequence are operably linked if the repressor protein binds to the nucleic acid sequence. Additionally, a protein may be operably linked to a first and a second nucleic acid sequence if the protein binds to the first nucleic acid sequence and so influences transcription of the second, separate nucleic acid sequence. Generally, "operably linked" means that the DNA sequences being linked are contiguous, although they need not be, and that a gene and a regulatory sequence or sequences (e.g., a promoter) are connected in such a way as to permit gene expression when the appropriate molecules (e.g., transcriptional activator proteins—transcription factors—or proteins which include transcriptional activator domains) are bound to the regulatory sequence or sequences.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, for example, hydroxyproline, gamma-carboxyglutamate, and O-phosphoserine, phosphothreonine.

An "amino acid analog" refers to a compound that has the same basic chemical structure as a naturally occurring amino acid, i.e., a carbon that is bound to a hydrogen, a carboxyl group, an amino group, and an R group (e.g., homoserine, norleucine, methionine sulfoxide, methionine methyl sulfonium), but that contains some alteration not found in a naturally occurring amino acid (e.g., a modified side chain). The term "amino acid mimetic" refers to chemical compounds that have a structure that is different from the general chemical structure of an amino acid, but that function in a manner similar to a naturally occurring amino acid. Amino acid analogs may have modified R groups (for example, norleucine) or modified peptide backbones, but retain the same basic chemical structure as a naturally occurring amino acid. In one embodiment, an amino acid analog is a D-amino acid, a beta-amino acid, or an N-methyl amino acid.

Amino acids and analogs are well known in the art. Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

The terms "polypeptide," "protein," and "peptide" are used herein interchangeably to refer to amino acid chains in which the amino acid residues are linked by peptide bonds or modified peptide bonds. The amino acid chains can be of any length of greater than two amino acids. Unless otherwise specified, the terms "polypeptide," "protein," and "peptide" also encompass various modified forms thereof. Such modified forms may be naturally occurring modified forms or chemically modified forms. Examples of modified forms include, but are not limited to, glycosylated forms, phosphorylated forms, myristoylated forms, palmitoylated forms, ribosylated forms, acetylated forms, etc. Modifications also include intra-molecular crosslinking and covalent attachment to various moieties such as lipids, flavin, biotin, polyethylene glycol or derivatives thereof, etc. In addition, modifications may also include cyclization, branching and cross-linking. Further, amino acids other than the conventional twenty amino acids encoded by genes may also be included in a polypeptide.

An "expression vector" or "vector" is a nucleic acid construct, generated recombinantly or synthetically, bearing a series of specified nucleic acid elements that enable transcription of a particular gene in a host cell. A vector is typically designed for transduction/transfection of one or more cell types. Typically, gene expression is placed under the control of certain regulatory elements, including constitutive or inducible promoters, tissue-preferred regulatory elements, and enhancers.

A "host cell" is any prokaryotic or eukaryotic cell that contains either a cloning vector or an expression vector. This term also includes those prokaryotic or eukaryotic cells that have been genetically engineered to contain the cloned gene(s) in the chromosome or genome of the host cell. In certain embodiments, a "host cell" or "transformed cell" refers to a cell into which (or into an ancestor of which) has been introduced, by means of recombinant DNA techniques, a polynucleotide molecule encoding (as used herein) a protein of the present invention.

By "fragment" is meant a portion (e.g., at least about 5, 10, 25, 50, 100, 125, 150, 200, 250, 300, 350, 400, or 500 amino acids or nucleic acids) of a protein or nucleic acid molecule that is substantially identical to a reference protein or nucleic acid and retains at least one biological activity of the reference. In some embodiments the portion retains at least 50%, 75%, or 80%, or more preferably 90%, 95%, or even 99% of the biological activity of the reference protein or nucleic acid described herein.

By "substantially identical" is meant a protein or nucleic acid molecule exhibiting at least 50% identity to a reference amino acid sequence (for example, any one of the amino acid sequences described herein) or nucleic acid sequence (for example, any one of the nucleic acid sequences described herein). Preferably, such a sequence is at least 60%, more preferably 80% or 85%, and most preferably 90%, 95% or even 99% identical at the amino acid level or nucleic acid to the sequence used for comparison.

Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between $e^{-3}$ and $e^{-100}$ indicating a closely related sequence.

The present invention is based, at least in part, on the discovery of an N-terminal tag sequence which aids in olfactory receptor trafficking. When expressed exogenously in mammalian cells, olfactory receptors (ORs) fail to traffic to the cell surface. This is a problem in the field as receptor ligands cannot be assayed unless the receptor is present on the cell surface. Either alone or in combination with chaperone proteins, this novel tag allows ORs assayed thus far to reach the cell surface.

This tag is cleaved off of the protein during protein processing. Because ORs on the cell surface will then be used to assay function of the OR (to screen for potential ligands), adding an N-terminal tag in many cases is not ideal as it may alter the structure of the protein. However, this tag succeeds in getting the OR out of the endoplasmic reticulum and Golgi, but is cleaved off before the OR reaches the cell surface. This is a unique feature, and this allows scientists to assay a surface-expressed OR that no longer has the tag (and therefore the tag cannot interfere with or modify ligand binding).

To assay whether the addition of a cleavable signal peptide could aid in OR surface expression, we added the 17 amino acid signal peptide from LRRC32 (which we named "Lucy," for its leucine repeats) to the N-terminus of 15 diverse ORs (murine ORs from both Class I and Class II, representing 11 different subfamilies, as well as 2 human ORs) and assayed for surface expression. We also combined our Lucy tag with both the Rho tag and the best practice in OR trafficking (co-expression with accessory proteins RTP1S, Ric8b and $G_{\alpha olf}$[18]) in order to assess the universal effects of this tag. See PCT Patent Application No. PCT/IB2013/002242 (incorporated by reference herein); U.S. patent application Ser. No. 14/037,606 (incorporated by reference herein); U.S. Provisional Patent Application No. 61/698,930 (incorporated by reference herein); and Shepard et al., 8(7) PLoS ONE e68758 (2013). In particular embodiments, we further report that the Lucy tag, in various combinations with a hemagglutinin (HA) tag, Rho tag and the accessory proteins, promotes surface expression of ORs, as well as other surfaced expressed proteins.

By allowing ORs to traffic to the cell surface, the present invention, in certain embodiments, greatly speeds the rate at which, for example, odorants and ligands can be identified. This can help basic science researchers to identify ligands for receptors and, in certain embodiments, can also help fragrance/flavor companies as they seek to develop new perfumes, etc.

Accordingly, in one aspect, the present invention provides nucleic acids/polynucleotide and amino acid/polypeptide sequences useful for improving/increasing protein expression on the cell surface. In several embodiments, the sequences are operably linked to the N-terminal end of the protein of interest. The nucleic acid sequence encoding the sequence tag and the protein comprise part of an expression vector. The protein is expressed with the N-terminal sequence tag. In certain embodiments, the sequences of the present invention can be used in conjunction with one or more chaperone or accessory proteins. In particular embodiments, the one or more chaperone/accessory proteins are encoded by the same vector or separate vectors. In other embodiments, the chaperone/accessory proteins are encoded the same vector that encodes the protein of interest.

Using the compositions and methods of the present invention, numerous proteins can be expressed on the surface of a host cell. Such proteins can be receptor or membrane proteins. The term "membrane protein," as used herein, refers to a protein that is attached to or associated with a membrane of a cell or an organelle. In several embodiments, the receptor proteins are olfactory receptors. Olfactory receptors can include, but are not limited to, Olfr78, Olfr51E2, mOREG (Olfr73), Olf145, Olfr691, Olfr52B2, Olfr99, Olfr693, Olfr805, Olfr1392, Olfr1393, Olfr90, Olfr545, Olfr985, and Olfr894. In other embodiments, the proteins of interest are taste receptors including type 1 (sweet) and type 2 (bitter) taste receptors. Examples of taste receptors include, but are not limited to, TAS1R1, TAS1R2, TAS1R3, TAS2R1, TAS2R2, TAS2R3, TAS2R4, TAS2R5, TAS2R6, TAS2R7, TAS2R8, TAS2R9, TAS2R10, TAS2R11, TAS2R12, TAS2R13, TAS2R14, TAS2R15, TAS2R16, TAS2R17, TAS2R18, TAS2R19, TAS2R20, TAS2R21, TAS2R22, TAS2R24, TAS2R25, TAS2R27, TAS2R28, TAS2R29, TAS2R30, TAS2R31, TAS2R32, TAS2R33, TAS2R34, TAS2R35, TAS2R36, TAS2R37, TAS2R38, TAS2R39, TAS2R40, TAS2R41, TAS2R42, TAS2R43, TAS2R45, TAS2R46, TAS2R50, TAS2R52, TAS2R53, TAS2R54, TAS2R55, TAS2R56, TAS2R57, TAS2R58, TAS2R59, TAS2R60, TAS2R62P, TAS2R63P, and TAS2R64P.

In other embodiments, the receptor or membrane proteins are G-protein coupled receptor proteins including, but not limited to, GPR160. GPCRs include, without limitation, serotonin and olfactory receptors, glycoprotein hormone receptors, chemokine receptors, adenosine receptors, biogenic amine receptors, melanocortin receptors, neuropeptide receptors, chemotactic receptors, somatostatin receptors, opioid receptors, melatonin receptors, calcitonin receptors, PTH/PTHrP receptors, glucagon receptors, secretin receptors, latrotoxin receptors, metabotropic glutamate receptors, calcium receptors, GABA-B receptors, pheromone receptors, histamine receptors, protease-activated receptors, rhodopsins and other G-protein coupled seven transmembrane segment receptors. The GPCRs can be associated with each other as homomeric or heteromeric dimers or as higher-order oligomers. Indeed, the compositions and methods of the present invention can be used to express any one of a number of proteins that do not traffic properly and/or do not already have a native signal sequence.

In a specific embodiment, the present invention provides the nucleotide sequence set forth in SEQ ID NO:1. In another embodiment, a nucleotide sequence encodes the amino acid sequence of SEQ ID NO:2. In yet another embodiment, the present invention provides an amino acid sequence set forth in SEQ ID NO:2. In another specific embodiment, the present invention provides the nucleotide sequence set forth in SEQ ID NO:13. In another embodiment, a nucleotide sequence encodes the amino acid sequence of SEQ ID NO:14. In yet another embodiment, the present invention provides an amino acid sequence set forth in SEQ ID NO:14

The present invention also provides an N-terminal amino acid sequence useful in trafficking proteins to the cell surface comprising SEQ ID NO:3. In certain embodiments, SEQ ID NO:3 can be referred to as the "Lucy tag." In another embodiment, the sequence further comprises an HA tag. The HA tag can comprise the amino acid sequence set forth in SEQ ID NO:6, or a nucleotide sequence encoding SEQ ID NO:6. In a specific embodiment, the sequence further comprises a Rho tag. The Rho tag can comprise the amino acid sequence set forth in SEQ ID NO:10. In a further embodiment, the sequence further comprises an HA tag and a Rho tag. The sequence can further comprise a linker between the HA tag and the Rho tag. The linker can be any linker that allows/promotes/increases surface expression of a protein of interest. An example of such a linker can include a 3 amino acid linker. In one embodiment, the linker comprises SEQ ID NO:8. Other linkers can be used and can include about 1 to about 20 amino acids. In certain embodiments, the Lucy tag is upstream of the HA tag, followed by the linker and the Rho tag.

In another embodiment, the Lucy sequence further comprises a Flag tag. The Flag tag can comprise the amino acid sequence set forth in SEQ ID NO:16, or a nucleotide sequence encoding SEQ ID NO:16. In a specific embodiment, the sequence further comprises a Rho tag. The Rho tag can comprise the amino acid sequence set forth in SEQ ID NO:10. In a further embodiment, the sequence further comprises a Flag tag and a Rho tag. The sequence can further comprise a linker between the Flag tag and the Rho tag. The linker can be any linker that allows/promotes/ increases surface expression of a protein of interest. An example of such a linker can include a 3 amino acid linker. In one embodiment, the linker comprises the amino acid sequence set forth in SEQ ID NO:8 (or a nucleotide sequence encoding the same). Other linkers can be used and can include about 1 to about 20 amino acids. In certain embodiments, the Lucy tag is upstream of the Flag tag, followed by the linker and the Rho tag.

In further embodiments, other epitope tags besides Flag and HA can be used with Lucy including, but not limited to, 6×His, glutathione-S-trasnferase (GST), c-myc, protein A, CD, polyglutamate, SBP-tag, Softag 1, Softag 3, TC tag (tetracysteine tag), V5, Xpress, BCCP, GFP, Nus-tag, Tioredoxin, and Avitag. Other examples include those based on interaction between streptavidin and biotin, maltose-binding peptide (MBP tag) and maltose, chitin-binding domain (CBD) and chitin, and the calmodulin-binding peptide that binds to calmodulin. Another type of tag is the S-peptide tag that binds to the S-protein derived from pancreatic RNase A. In particular embodiments, such tags can also be cleavable, by the protease enterokinase, for example, or it can be self-cleaving. Such tags can be used in conjunction with Rho (or not), linkers, etc., as described in the above embodiments for HA and/or Flag.

The present invention also provides an N-terminal amino acid sequence useful in trafficking proteins to the cell surface comprising an amino acid sequence substantially identical to SEQ ID NO:3. In one embodiment, the sequence has at least about 85% identity to SEQ ID NO:3. In other embodiments, the sequence has at least about 88%, at least about 90%, at least about 91%, at least about 92%, at least about 93%, at least about 94%, or at least about 95% identity to SEQ ID NO:3 (Lucy tag). Indeed, the present invention contemplates one or more amino acid substitutions to the Lucy tag. Such substitutions can be conservative substitutions. One of ordinary skill in the art can substitute amino acids based on similar side chain polarity (e.g., alanine and cysteine are both non-polar) and/or side chain charge (e.g., isoleucine and leucine are both neutral). In most embodiments, the Lucy tag retains its leucine rich nature.

In another embodiment, the N-terminal amino acid sequence useful in trafficking proteins to the cell surface further comprises an HA tag. In another embodiment, the sequence further comprises a Rho tag. In a further embodiment, the sequence further comprises an HA tag and a Rho tag. In a specific embodiment, the sequence further comprises a linker between the HA tag and the Rho tag.

In another aspect, the present invention provides systems for increasing surface expression of proteins. In one embodiment, the system comprises: (a) a vector comprising (i) a nucleotide sequence described herein or (ii) a nucleotide sequence encoding an amino acid sequence described herein; and (b) a vector encoding a chaperone protein that aids in expression, signaling and/or trafficking of the protein to the cell surface. In particular embodiments, the protein is an olfactory receptor. In other embodiments, the protein is a GPCR. The system can be used to clone in the sequence encoding a protein of interest into the vector of step (a). In specific embodiments, the chaperone protein is a receptor trafficking protein. The receptor trafficking protein can be selected from the group consisting of RTPL1, RTP1S, and RTP2. In another embodiment, the chaperone protein is Receptor Expressing Enhancing Protein (REEP). In yet another embodiment, the chaperone protein is β-adrenergic receptor. The chaperone can also be heat shock protein 70 homolog. In a specific embodiment, the chaperone protein is Resistance to Inhibitors of Cholinesterase 8 homolog B (Ric8b). The chaperone protein can also be Olfactory G-protein (Gαolf). The system can utilize any combination of the foregoing including, but not limited to, RTP1S, Ric8b and Gαolf. A vector can encode one or more chaperone proteins or multiple vectors can be used. In certain embodiments, the system further comprises a cell line. In a specific embodiment, the cell line may comprise HEK293T cells.

The present invention further provides a system for increasing surface expression of proteins comprising: (a) a vector comprising a nucleotide sequence encoding SEQ ID NO:3; (b) a vector encoding RTP1S; (c) a vector encoding Ric8b; and (d) a vector encoding Gαolf. In another embodiment, the system comprises the vector of step (a) and (b) one or more of a vector encoding RTP1S, a vector encoding Ric8b, and/or a vector encoding Gαolf. It is understood that the nucleotide sequence encoding the protein of interest can be cloned into the vector of step (a). In particular embodiments, the Lucy tag is operably linked to the N-terminal end of the protein of interest. Alternatively, a vector can encode one or more chaperone/accessory proteins. Further, a single vector can be used to encode SEQ ID NO:3, the protein of interest and one or more chaperone/accessory proteins. In an alternative embodiment, the vector of step (a) further comprises a nucleotide sequence encoding an HA tag. In another embodiment, the vector of step (a) further comprises a nucleotide sequence encoding Rho tag. In yet another embodiment, the vector of step (a) further comprises a nucleotide sequence encoding a HA tag and a Rho tag. Further, the vector of step (a) can comprise a linker between the HA tag and the Rho tag.

In yet another alternative embodiment, the vector of step (a) further comprises a nucleotide sequence encoding a Flag tag. In another embodiment, the vector of step (a) further comprises a nucleotide sequence encoding Rho tag. In yet another embodiment, the vector of step (a) further comprises a nucleotide sequence encoding a Flag tag and a Rho tag. Further, the vector of step (a) can comprise a linker between the Flag tag and the Rho tag.

The present invention also provides a system for increasing surface expression of proteins comprising: (a) a vector comprising a nucleotide sequence encoding SEQ ID NO:2 or SEQ ID NO:14; (b) a vector encoding RTP1S; (c) a vector encoding Ric8b; and (d) a vector encoding Gαolf. In another embodiment, the system comprises the vector of step (a) and (b) one or more of a vector encoding RTP1S, a vector encoding Ric8b, and/or a vector encoding Gαolf. The nucleotide sequence encoding the protein of interest can be cloned into the vector of step (a). In particular embodiments, the protein is a receptor protein, which can include, but is not limited, to GPCRs and olfactory receptors. In another embodiment, a system for increasing surface expression of olfactory receptors comprises: (a) a vector comprising a nucleotide sequence encoding SEQ ID NO:2 or SEQ ID NO:14; (b) a vector encoding RTP1S; (c) a vector encoding Ric8b; and (d) a vector encoding Gαolf. In another embodiment, the system comprises the vector of step (a) and (b) one or more of a vector encoding RTP1S, a vector encoding Ric8b, and/or a vector encoding Gαolf. The nucleotide sequence encoding the olfactory receptor can be cloned into the vector of step (a). In particular embodiments, the Lucy tag is operably linked to the N-terminal end of the protein of interest/olfactory receptor.

Olfactory receptors (ORs) are G protein-coupled receptors that detect odorants in the olfactory epithelium, and comprise the largest gene family in the genome. Identification of OR ligands typically requires OR surface expression in heterologous cells; however, ORs rarely traffic to the cell surface when exogenously expressed. Therefore, most ORs are orphan receptors with no known ligands. To date, studies have utilized non-cleavable rhodopsin (Rho) tags and/or chaperones (i.e., Receptor Transporting Protein, RTP1S, Ric8b and Gαolf) to improve surface expression. However, even with these tools, many ORs still fail to reach the cell surface. We used a test set of fifteen ORs to examine the effect of a cleavable leucine-rich signal peptide sequence (Lucy tag) on OR surface expression in HEK293T cells. We report here that the addition of the Lucy tag to the N-terminus increases the number of ORs reaching the cell surface to 7 of the 15 ORs (as compared to 3/15 without Rho or Lucy tags). Moreover, when ORs tagged with both Lucy and Rho were co-expressed with previously reported chaperones (RTP1S, Ric8b and Gαolf), we observed surface expression for all 15 receptors examined. In fact, two-thirds of Lucy-tagged ORs are able to reach the cell surface synergistically with chaperones even when the Rho tag is removed (10/15 ORs), allowing for the potential assessment of OR function with only an 8-amino acid Flag tag on the mature protein. As expected for a signal peptide, the Lucy tag was cleaved from the mature protein and did not alter OR-ligand binding and signaling. Our studies demonstrate that widespread surface expression of ORs can be achieved in HEK293T cells, providing promise for future large-scale deorphanization studies. Furthermore, as described herein in FIGS. 1-6, the Lucy-HA tag performs as well as or better than Lucy-Flag, and that the Lucy tag (in addition to aiding surface expression of olfactory receptors, or ORs) also works for an unrelated G-protein coupled receptor, Gpr160. This shows that the Lucy tag can be used to aid in surface trafficking for receptors beyond the OR family.

EXAMPLES

The following examples are put forth so as to provide those of ordinary skill in the art with a complete disclosure and description of how the compounds, compositions, articles, devices, and/or methods described and claimed herein are made and evaluated, and are intended to be purely illustrative and are not intended to limit the scope of what the inventors regard as their invention. Efforts have been made to ensure accuracy with respect to numbers (e.g., amounts, temperature, etc.) but some errors and deviations should be accounted for herein. Unless indicated otherwise, parts are parts by weight, temperature is in degrees Celsius or is at ambient temperature, and pressure is at or near atmospheric. There are numerous variations and combinations of reaction conditions, e.g., component concentrations, desired solvents, solvent mixtures, temperatures, pressures and other reaction ranges and conditions that can be used to optimize the product purity and yield obtained from the described process. Only reasonable and routine experimentation will be required to optimize such process conditions.

Olfactory receptors (ORs) are G protein-coupled receptors that detect odorants in the olfactory epithelium, and comprise the largest gene family in the genome. Identification of OR ligands typically requires OR surface expression in heterologous cells; however, ORs rarely traffic to the cell surface when exogenously expressed. Therefore, most ORs are orphan receptors with no known ligands. To date, studies have utilized non-cleavable rhodopsin (Rho) tags and/or chaperones (i.e., Receptor Transporting Protein, RTP1S, Ric8b and Gαolf) to improve surface expression. However, even with these tools, many ORs still fail to reach the cell surface. We used a test set of fifteen ORs to examine the effect of a cleavable leucine-rich signal peptide sequence (Lucy tag) on OR surface expression in HEK293T cells. We report here that the addition of the Lucy tag to the N-terminus increases the number of ORs reaching the cell surface to 7 of the 15 ORs (as compared to 3/15 without Rho or Lucy tags). Moreover, when ORs tagged with both Lucy and Rho were co-expressed with previously reported chaperones (RTP1S, Ric8b and Gαolf), we observed surface expression for all 15 receptors examined. In fact, two-thirds of Lucy-tagged ORs are able to reach the cell surface synergistically with chaperones even when the Rho tag is removed (10/15 ORs), allowing for the potential assessment of OR function with only an 8-amino acid Flag tag on the mature protein. As expected for a signal peptide, the Lucy tag was cleaved from the mature protein and did not alter OR-ligand binding and signaling. Our studies demonstrate that widespread surface expression of ORs can be achieved in HEK293T cells, providing promise for future large-scale deorphanization studies.

Materials and Methods

Reagents and Antibodies.

Polyclonal (F7425) and M2 monoclonal (F1804) Flag antibodies and M2 Flag beads were purchased from Sigma (St. Louis, Mo.). The monoclonal HA antibody (3F10) was purchased from Roche (Indianapolis, Ind.) and the β-actin antibody was purchased from Abcam (Cambridge, Mass.). Alexa-conjugated fluorescent secondary antibodies were purchased from Invitrogen (Carlsbad, Calif.). HRP-conjugated secondary antibodies were purchased from Jackson ImmunoResearch Labs (West Grove, Pa.). The Dual-Luciferase Reporter Assay kit was purchased from Promega (Madison, Wis.). The odorants used in this study, isovaleric acid and eugenol, were also purchased from Sigma.

OR Constructs and Cloning.

The mOR-EG full-length construct, containing N-terminal Flag/Rho tags, was a kind gift from Kazushige Touhara (Univ. of Toyko) [22]. To clone the full-length sequences of the other ORs tested into the "Rho-OR" vector, the sequence encoding mOR-EG was excised from its parent vector (pME18S) and PCR products containing the full-length sequence of other ORs of interest were ligated into the corresponding sites in this vector. ORs were ligated in frame with an upstream start site, such that they incorporated sequences encoding N-terminal Flag and Rho tags. Full-length human OR51E2 and OR52B2 were amplified by PCR from human DNA (using primers which added appropriate restriction sites), taking advantage of the fact that ORs do not contain introns. The constructs containing murine Olfr78 (MOR18-2), Olfr90 (MOR256-21), Olfr1392 (MOR256-25), Olfr1393 (MOR256-24) and mOR-EG have been previously described [31]. The other full-length ORs were amplified using primers which added appropriate restriction sites from either mouse genomic DNA or from kidney RNA after performing RT (Olfr145 (MOR161-6, K21), Olfr99 (MOR156-1), Olfr394 (MOR135-8), Olfr545 (MOR42-1, S50), Olfr691 (MOR31-6), Olfr693 (MOR283-8), Olfr805 (MOR110-4), and Olfr985 (MOR171-4)). All constructs used in this study contain a Flag tag for detection purposes but will be referenced based on their other N-terminal tags for simplicity. All constructs were sequenced to confirm identity.

The Lucy tag (atgagaccccagatcctgctgctcctggccctgctgac-cctaggcctggct) (SEQ ID NO:4) was added to the original (Rho-OR) vector for Olfr691 using overlap-extension PCR [32] to obtain a Lucy-Rho-OR. Subsequently, Olfr691 was excised from the Lucy-Rho vector, and the other ORs were excised from the original parent vector (Rho-OR) using the same restriction sites. The other ORs were then subcloned into the Lucy-Rho vector by ligation.

The Rho tag was deleted from both the Rho-Olfr78 and Lucy-Rho-Olfr78 constructs to obtain the OR or Lucy-OR constructs using PCR-mediated deletion [33]. Subsequently, Olfr78 was excised from the vectors, and the other ORs were excised from the original parent vector (Rho-OR) using the same restriction sites and then subcloned into the OR and Lucy-OR vectors by ligation.

To assay Lucy cleavage, an HA tag was added to the extreme N-terminus of the Lucy-Rho construct for Olfr691 using overlap-extension PCR [32], yielding an HA-Lucy-Flag-Rho-Olfr691 construct. As a control, an HA tag was also added to the extreme N-terminus of the Rho construct for Olfr691, yielding an HA-Flag-Rho-Olfr691 construct.

Immunofluorescence.

Figure 2:
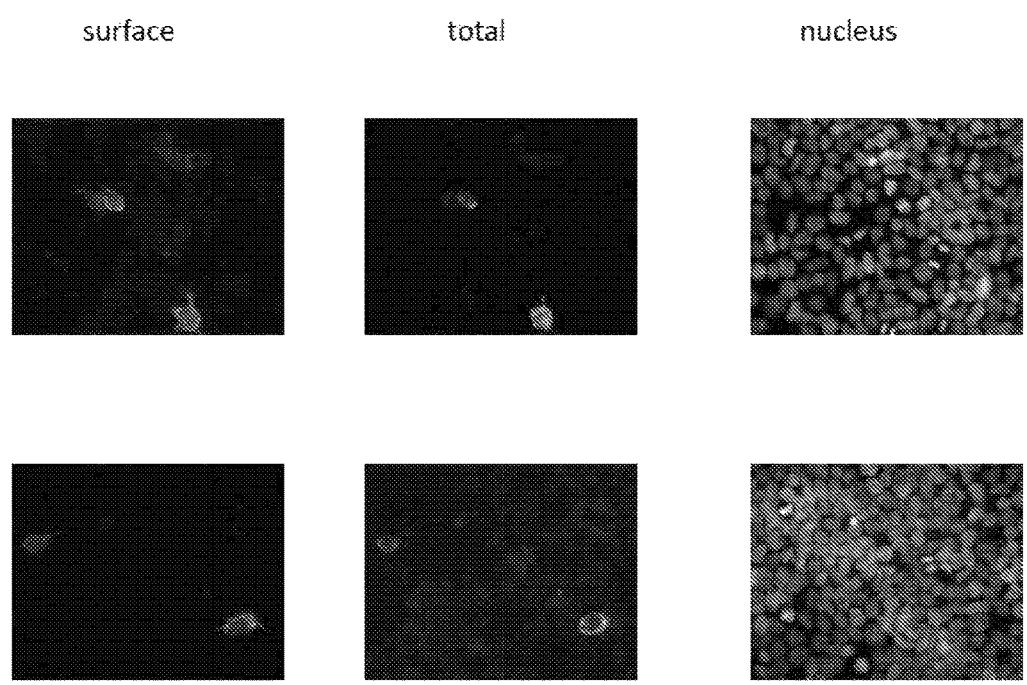
FIG. 2. Two examples of Lucy-Flag-Rho-691 stained for surface Flag (unpermeabilized cells), total Flag and with a nuclear stain.
Figure 3:
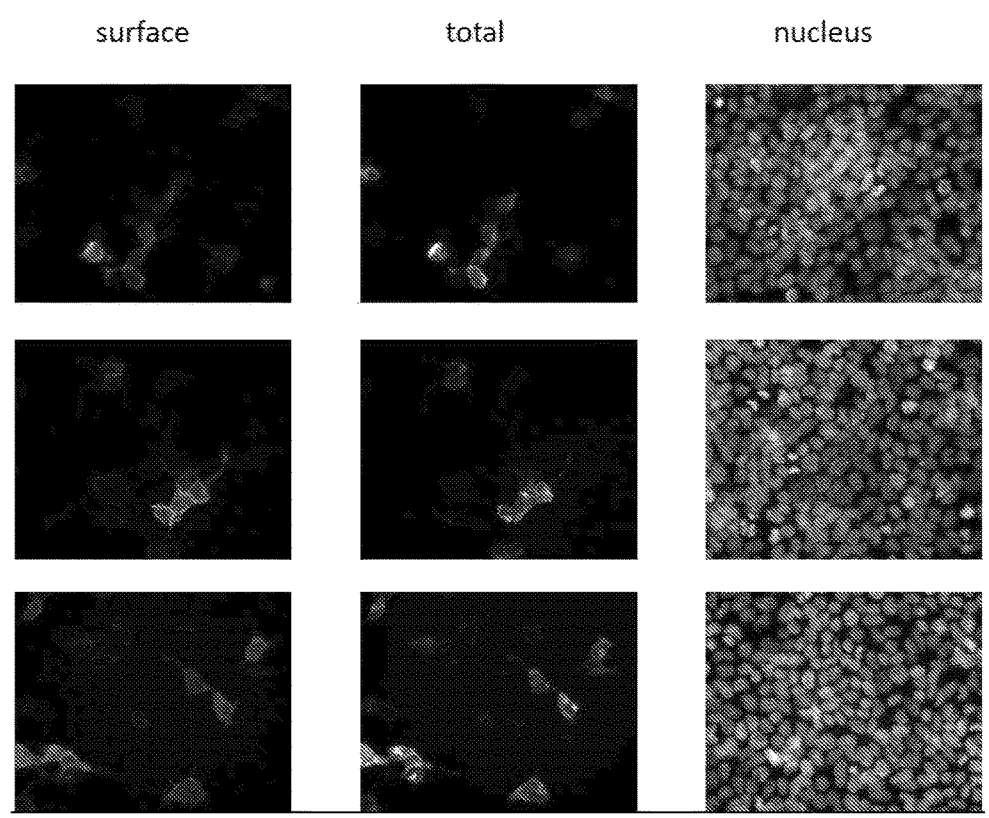
FIG. 3. Three examples of Lucy-HA-Rho-691 co-transfected with RTP and Ric8b and stained for surface HA (unpermeabilized cells), total HA and with a nuclear stain.
Figure 5:
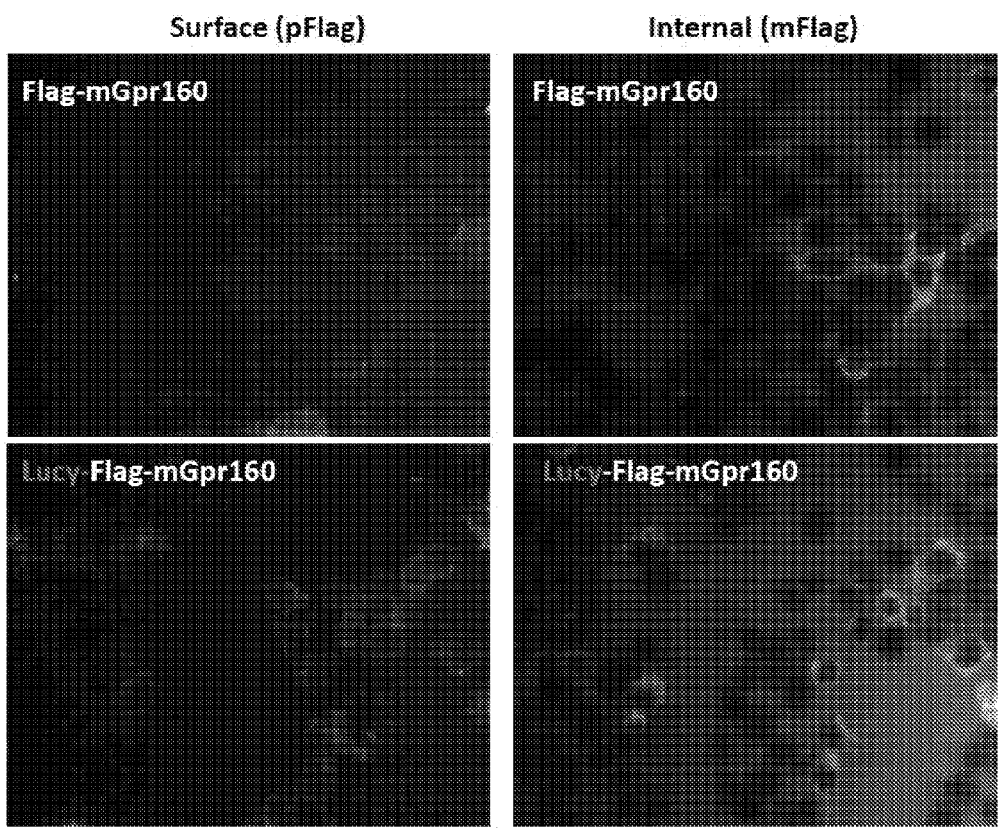
FIG. 5. The Lucy tag promotes surface expression of murine Gpr160 in HEK293T cells.
Figure 6:
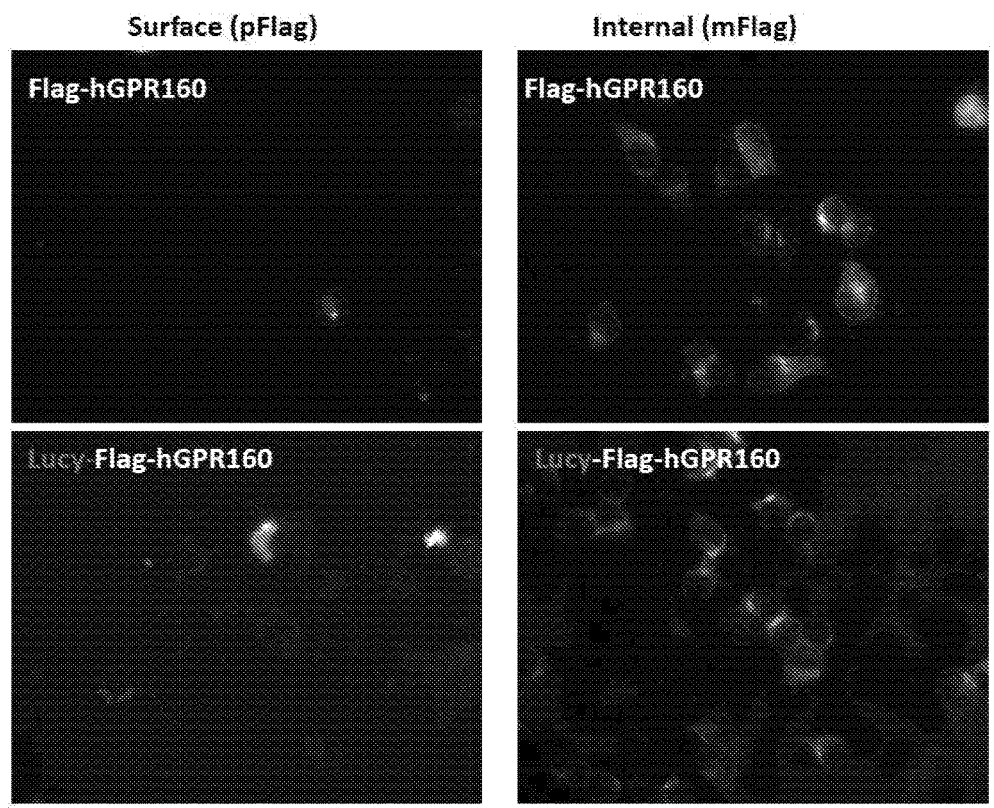
FIG. 6. The Lucy tag promotes surface expression of human GPR160 in HEK293T cells.
Figure 8:
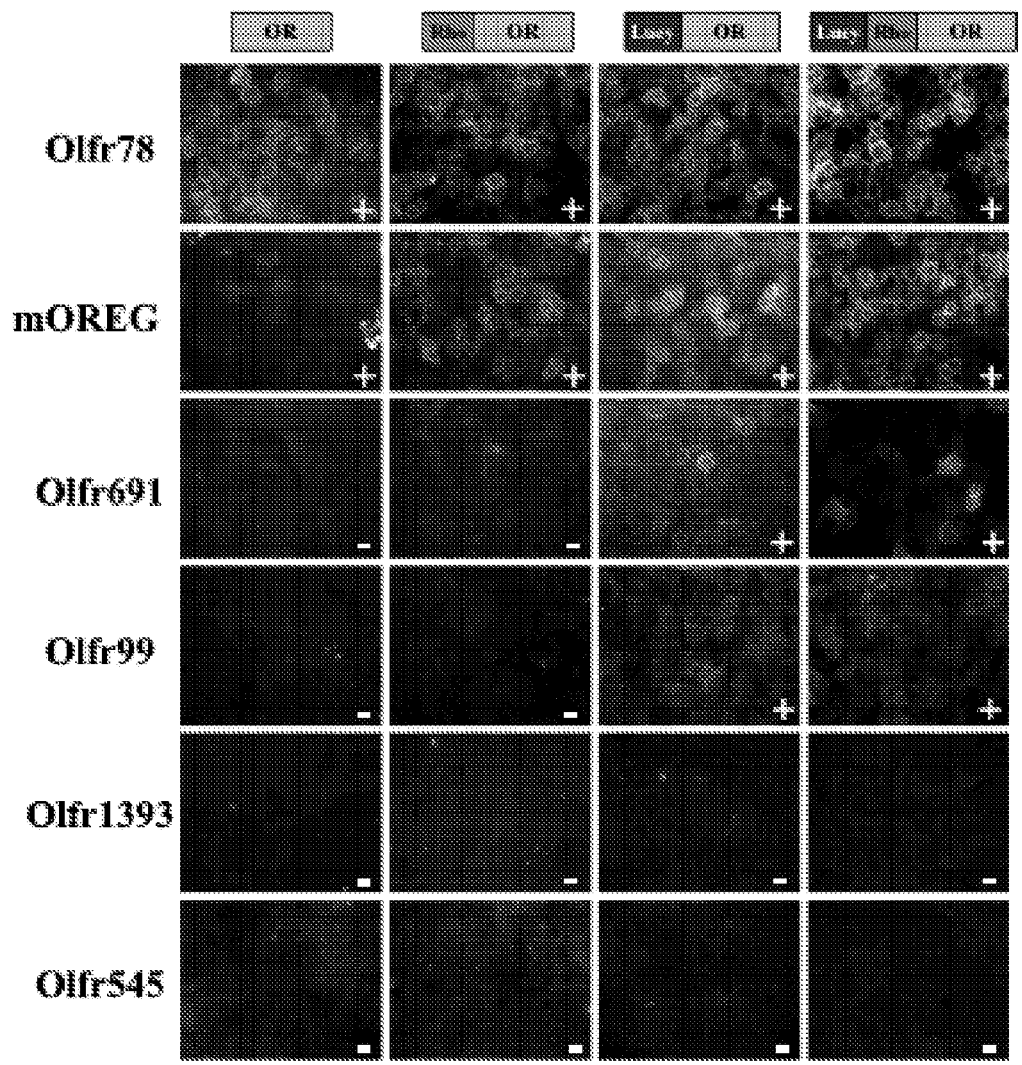
FIG. 8. The Lucy tag aids in surface expression of some ORs in the absence of accessory proteins or the Rho tag. ORs were cloned and expressed in HEK293T cells without Rho or Lucy tags (OR), with a Rho tag (Rho-OR), with the Lucy tag (Lucy-OR) or with both the Lucy and Rho tags (Lucy-Rho-OR). The cells were then surface labeled with a Flag antibody to detect membrane-associated OR. Images were taken for each OR at equal exposure for all conditions. To assess OR surface expression, the entirety of each coverslip was systematically scanned and scored based on detectable surface immunofluorescence. A '+' was scored for those ORs whose surface expression was detectable in >90% of all fields of view while ORs received an '*' if surface expression was found in <50% of all fields of view. A complete lack of detectable surface expression was scored as a '−'. Results for 6 representative ORs are shown in FIG. 15 and the results for all ORs tested are summarized in Table 1.
Figure 9:
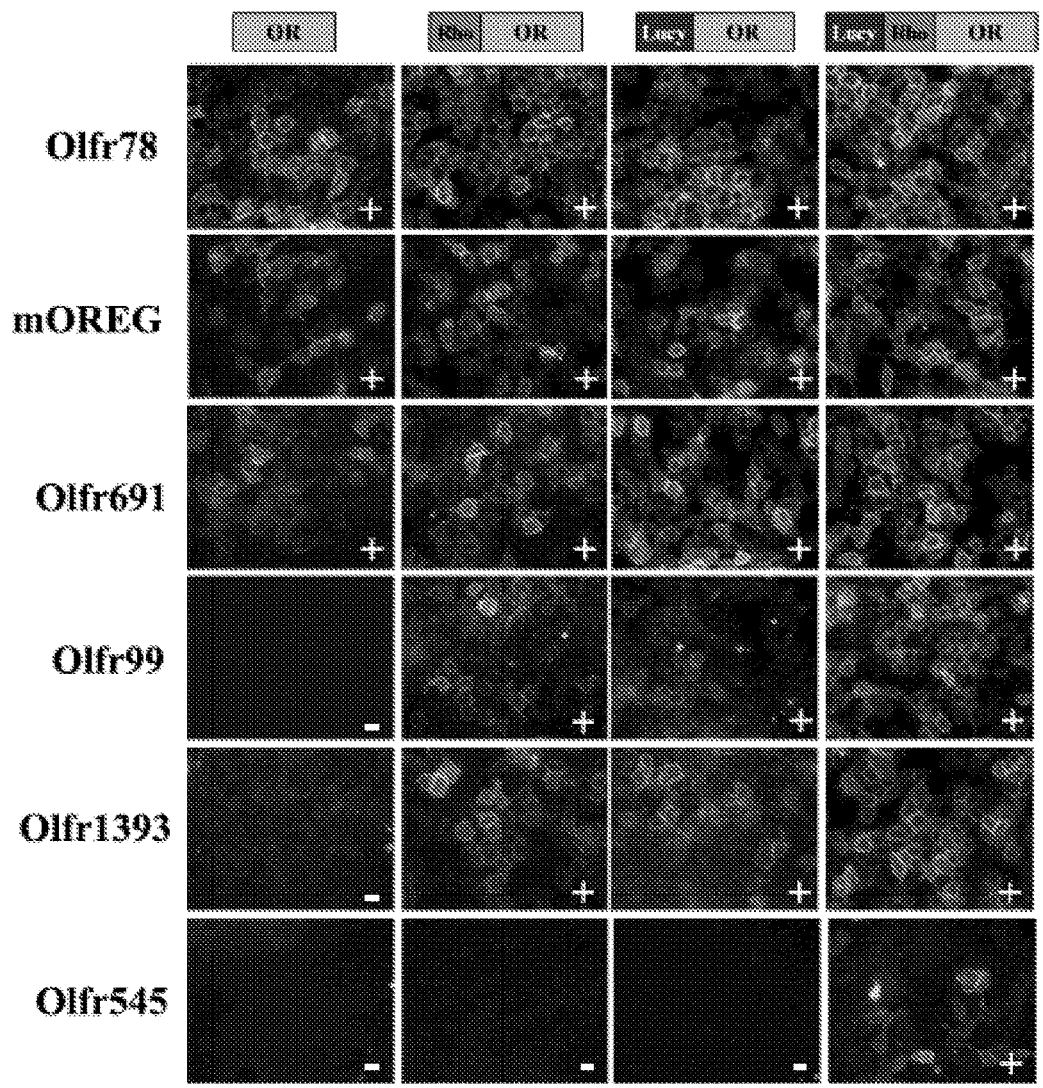
FIG. 9. The Lucy tag works synergistically with accessory proteins and tags to promote surface expression of ORs.

HEK293T cells were seeded onto 18-mm coverslips coated with poly-L-lysine and transfected with OR constructs with or without accessory proteins (Lipofectamine 2000, Invitrogen). Flag-tagged OR trafficking was assayed using surface immunocytochemistry, as previously described [5]. Briefly, live, non-permeabilized cells at 4° C. were exposed to a rabbit polyclonal anti-Flag antibody in PBS with 0.1% BSA. Subsequently, cells were washed, fixed with 4% paraformaldehyde, permeabilized (0.3% Triton X-100) and then exposed to a mouse monoclonal (M2) anti-Flag antibody. As the external Flag epitope (surface Flag) epitope is 'blocked' after binding to the polyclonal Flag antibody, the monoclonal Flag antibody detects only the internal population of ORs. Control experiments where the cells were surface labeled with the polyclonal Flag antibody followed by another surface label with the monoclonal Flag antibody confirmed that 100% of the external Flag epitopes were bound by the polyclonal antibody, as no subsequent labeling was seen with the second surface label. Fluorescent secondary antibodies reported the localization of the polyclonal and monoclonal Flag-tags. Cells were visualized for epifluorescence using a Zeiss Axiophot microscope (Thornwood, N.Y.). Images were taken with a CoolSnap Digita Camera (Photometrics, Tucson, Ariz.) and IP Labs software (Biovision, Exton, Pa.). For some experiments, a total of 0.8 µg of accessory plasmids (pcDNA3-RTP1S (modified from RTP1L, kind gift from S. Firestein, Columbia Univ.), pCMV Sport6-Ric8b (purchased from Open Biosystems), and pcDNA3.1-$G_{\alpha olf}$ (subcloned from a pGEMHE2 $G_{\alpha olf}$ construct, kind gift from S. Firestein, Columbia Univ.)) or 0.8 µg of an empty pcDNA4.1 vector (OR alone) were co-transfected along with 0.8 µg of the OR. In FIGS. 1 and 2, the immunofluorescent images shown in each row (OR, Rho-OR, Lucy-OR and Lucy-Rho-OR with and without accessory proteins) were transfected and processed simultaneously and image exposures remained constant for each OR. Images represent representative fields of view from at least 4 independent experiments. To assess OR surface expression, the entirety of each coverslip was systematically scanned and scored based on detectable surface immunofluorescence. A '+' was scored for those ORs whose surface expression was detectable in >90% of all fields of view while ORs received an '*' if surface expression was found in <50% of all fields of view. A complete lack of detectable surface expression was scored as a '−'. To quantitate cell surface expression using ImageJ (FIG. 14), the background was subtracted from the surface labeled Olfr691 images and the mean fluorescence intensity was measured. The mean intensity was normalized to the mean intensity of the corresponding binary nuclear image, to control for cell number.

ORs were cloned and co-expressed in HEK293T cells without Rho or Lucy tags (OR), with a Rho tag (Rho-OR), with the Lucy tag (Lucy-OR) or with both the Lucy and Rho tags (Lucy-Rho-OR) along with (or without) the chaperone proteins, RTP1S, Ric8b and $G_{\alpha olf}$. The cells were then surface labeled with a Flag antibody to detect membrane-associated OR. Images were taken for each OR at equal exposure for all conditions. To assess OR surface expression, the entirety of each coverslip was systematically scanned and scored based on detectable surface immunofluorescence. A '+' was scored for those ORs whose surface expression was detectable in >90% of all fields of view while ORs received an '*' if surface expression was found in <50% of all fields of view. A complete lack of detectable surface expression was scored as a '−'. Results for 6 representative ORs are shown in FIG. 16 and the results for all ORs tested are summarized in Table 1.

Enzyme-Linked Immunosorbent Assay (ELISA).

ELISA measurements in HEK 293T cells transfected with various constructs were performed as previously described [5,34]. Wells for ELISA were assayed in quadruplicate. Briefly, transfected cells seeded in a 96 well plate were fixed and permeabilized. OR-expressing cells were probed with the polyclonal Flag antibody and detected with anti-rabbit HRP-conjugated secondary antibody. HRP levels were detected with 1-Step Ultra TMB (3,3',5,5'-tetramethylbenzidine) (Thermo Scientific, Rockville, Ill.).

Immunoprecipitation and Western Blotting.

HEK293T cells in 35-mm dishes were transfected for 24 h with either the Rho-OR or Lucy-Rho-OR constructs and lysed in lysis buffer containing 1% NP-40, 150 mM NaCl, 50 mM Tris and 1 mM EDTA on ice for 30 min. The lysate was cleared by centrifugation at 16,000×g for 30 min at 4° C. and 10% of the lysate was collected in Laemmli sample buffer for later analysis. Flag-tagged ORs were then immunoprecipitated from the remaining lysate using M2 monoclonal Flag beads. Both the immunoprecipitated fraction (B) and unbound fractions (UB) were lysed in Laemmli sample buffer and equal amounts were loaded on a gel along with the input lysate. Proteins were transferred to a nitrocellulose membrane and immunoblotted with the polyclonal Flag antibody using standard procedures. The input lysate membrane was stripped and reprobed for β-actin to ensure equal loading.

Luciferase Assay.

The luciferase assay was performed as previously described [5]. Briefly, ORs were transfected into HEK293T cells along with constructs encoding for CREB-dependent luciferase (Firefly) and a constitutively expressed luciferase (Renilla). OR activation leads to a rise in cAMP which drives an increase in Firefly luciferase expression. Firefly activity is normalized to the activity of the Renilla luciferase to control for variation in cell number and transfection efficiency. Data were collected using a FLUOstar Omega automated platereader (BMG LabTech, Cary, N.C.). For some experiments, RTP1S was also transfected.

Statistical Analysis.

One-way ANOVA analysis followed by the Student-Newman Keuls test was performed on the luciferase reporter assay to compare the doses of isovaleric acid (0.1-5 mM) or eugenol (100-300 μM) to the non-treated control (0 μM). As each condition was performed in triplicate, the analyses were done with an n=3, and P values ≤0.05 were deemed significant. One-way ANOVE followed by Student-Newman Keuls was also used to analyze the surface expression data in FIG. 14. A Student T-Test was performed on the ELISA to assess the significance of the increased protein expression (Control construct vs. Lucy construct for each OR, n=4 for each condition). P values ≤0.05 were deemed significant. In both the luciferase reporter assay and the ELISA, the error bars represent the SEM.

Results

Surface Expression of ORs with and without Rhodopsin Tags.

Figure 13A:
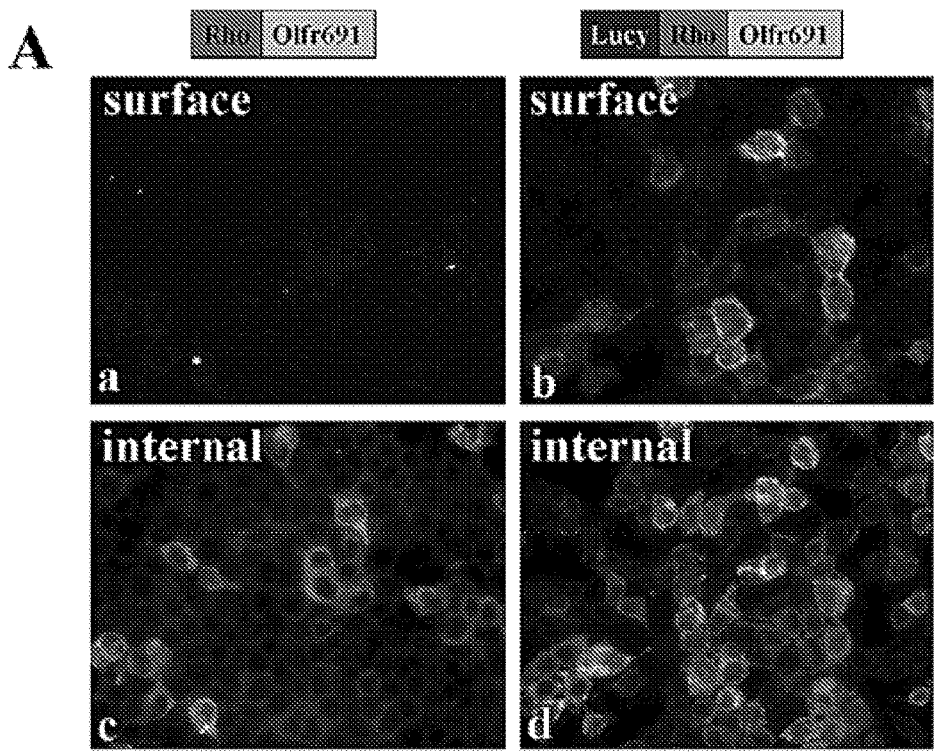
FIG. 13. The Lucy tag promotes detectable surface expression of olfactory receptors in the absence of accessory proteins. (A and B) HEK293T cells were transfected for 24 h with Rho-tagged or Lucy-Rho-tagged Olfr691 (A) or its human homologue, hOR52B2 (B). Cells were surface labeled with a polyclonal Flag antibody to detect surface-associated OR (a and b) and then fixed, permeabilized and stained with a monoclonal Flag antibody to detect the internal OR population (c and d). Both Olfr691 and hOR52B2 traffic to the surface with but not without the Lucy tag.
Figure 13B:
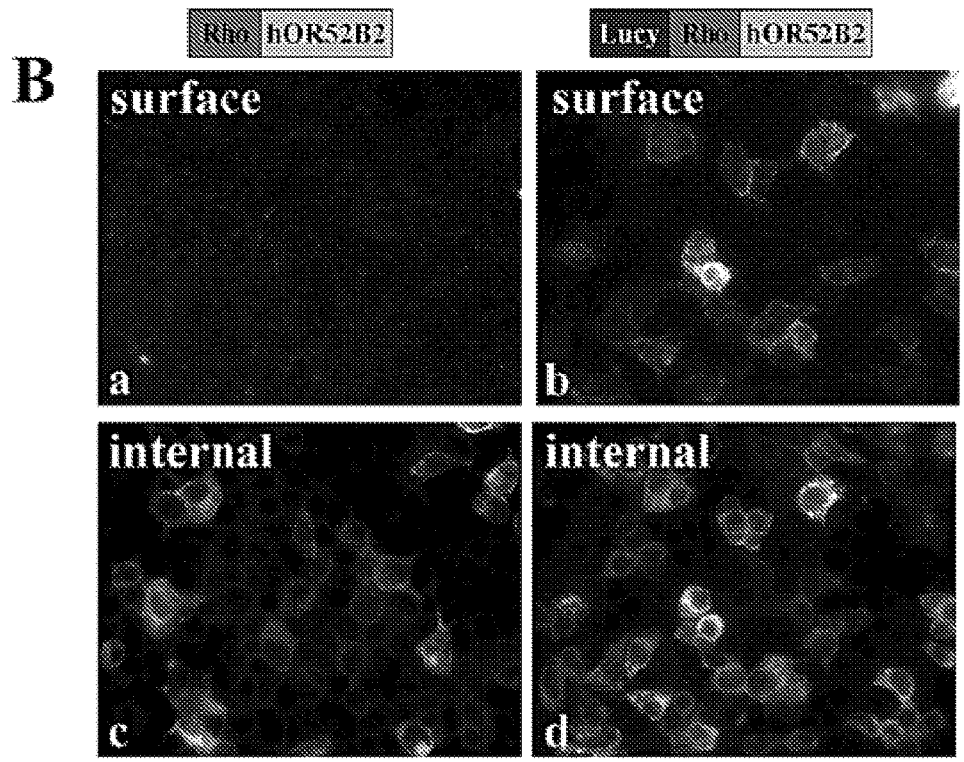

Many ORs remain orphan receptors due to their inability to traffic in in vitro assays. To establish the trafficking ability of a varied group of ORs, we cloned 15 diverse ORs, the majority of which are orphan receptors which have not been previously reported to reach the cell surface. Live, non-permeabilized HEK 293T cells were surface labeled with a Flag antibody to detect membrane associated receptor and OR surface expression was scored based on detectable surface immunofluorescence. A '+' was scored for those ORs whose surface expression was detectable in >90% of all fields of view, while ORs received an '*' if surface expression was found in <50% of all fields of view (n=4). A complete lack of detectable surface expression was scored as a '−'(Table 1). Examples of OR surface expression (or absence) can be found in FIG. 15, and the results for all ORs are summarized in Table 1 (Columns 1, 3, 5, and 7). ORs were cloned both with and without a 22-amino acid Rho tag (an N-terminal tag often used to aid in surface trafficking of ORs in vitro [15]). A small number of ORs were detected on the cell surface even in the absence of the Rho tag (Table 1, column 1). Surprisingly, the addition of the Rho tag (Table 1, column 3) had little effect on the number of ORs which reached the cell surface. Importantly, 'internal' Flag staining was consistently seen for every construct (as shown in FIG. 13 for Rho-Olfr691 and Rho-hOR52B2).

TABLE 1

Trafficking of olfactory receptors in the absence and presence of RTP1S, Ric8b and Gαolf (accessory factors).

| Columns | 1 | 2 | 3 | 4 | 5 | 6 | 7 | 8 |
|---|---|---|---|---|---|---|---|---|
| Flag-tagged Olfactory Receptors | OR | | Rho-OR | | Lucy-OR | | Lucy-Rho-OR | |
| Chaperones? | None | RTP1S, Ric8b, Gαolf | None | RTP1S, Ric8b, Gαolf | None | RTP1S, Ric8b, Gαolf | None | RTP1S, Ric8b, Gαolf |
| Olfr78 | + | + | + | + | + | + | + | + |
| hOR51E2 | + | + | + | + | + | + | + | + |
| mOREG | + | + | + | + | + | + | + | + |
| Olfr145 | * | + | + | + | + | + | + | + |
| Olfr691 | − | + | − | + | + | + | + | + |
| hOR52B2 | − | − | − | − | + | + | + | + |
| Olfr99 | − | − | − | − | + | + | + | + |
| Olfr693 | − | − | − | + | − | − | − | + |
| Olfr805 | − | − | − | − | − | − | * | + |
| Olfr1392 | − | − | − | + | − | + | − | + |
| Olfr1393 | − | − | − | + | − | + | − | + |
| Olfr90 | − | − | − | + | − | + | − | + |
| Olfr545 | − | − | − | − | − | − | − | + |
| Olfr985 | − | − | − | − | − | − | − | + |
| Olfr394 | − | − | − | − | − | − | − | * |

−: No detectable OR surface expression
+: OR surface expression detected in the majority of fields of view (>90% of all fields of view)
*: OR surface expression detected in a minority of fields of view (<50% of all fields of view)

A Cleavable Signal Peptide Enhances Olfactory Receptor Surface Expression.

Recently, a 17-amino acid N-terminal signal peptide on Leucine Rich Repeat Containing 32 (LRRC32) was found to be required for proper cell surface expression of LRRC32 in regulatory T cells and HEK293T cells. This sequence (MRPQILLLLALLTLGLA) (SEQ ID NO:3) represents a classic cleavable signal peptide that serves to mediate the integration of proteins into the ER membrane [28]. We hypothesized that the addition of this cleavable peptide, known here as "Lucy" for its leucine rich repeat regions, could also promote surface expression of olfactory receptors; the use of a cleavable signal sequence would be advantageous, as it would potentially aid in trafficking without adding additional amino acids to the mature OR protein. To determine whether the Lucy tag can promote OR surface trafficking, we added the Lucy sequence to the N-terminus of the 15 ORs and found that a total of 7 ORs were able to reach the cell surface (Table 1, column 5). To determine if the Lucy and Rho tags may have an additive effect, we assayed for the surface expression of ORs tagged with both Lucy and Rho and found that 8 ORs reached the cell surface (Table 1, column 7).

Lucy Works Synergistically with RTP1s and Other Accessory Proteins to Promote OR Surface Expression.

Previously, studies have found that the Rho tag works in synergism with RTP1S, Ric8b and $G_{\alpha olf}$ to induce the greatest functional expression of ORs to date [18]. Therefore, we wondered if the Lucy tag could also work synergistically with these accessory proteins. To test for this, OR constructs (both with and without the Rho and Lucy tags) were co-transfected into cells along with RTP1S, Ric8b, $G_{\alpha olf}$ and assayed for detectable surface expression. Examples can be seen in FIG. 16 and the results for all ORs are summarized in Table 1 (Columns 2, 4, 6, and 8). For the untagged ORs, co-expression of the accessory proteins allowed for surface expression of 5 ORs (Table 1, column 2). When Rho-tagged ORs were co-expressed with accessory proteins (currently the best practice for achieving OR surface expression [18]), 9 ORs were found on the cell surface (Table 1, column 4). When Lucy-tagged ORs were co-expressed with the accessory proteins, 10 ORs were found on the cell surface (Table 1, column 6). These data confirm that the Rho tag can work synergistically with accessory proteins to promote proper expression [18], and demonstrate that the same is true for the Lucy tag (Table 1). Importantly, when we used Lucy-Rho-tagged ORs together with known chaperones (RTP1S/Ric8b/$G_{\alpha olf}$), all 15 ORs were detected on the cell surface (Table 1, Column 8).

It is worth noting that although the Rho tag, the Lucy tag, and OR chaperones all promote surface expression of some (but not all) ORs tested, they seem to promote expression of different populations of ORs. For example, Olfr99 and hOR52B2 require the Lucy tag for surface expression, but not the combination of accessory proteins or the Rho tag (Table 1). On the other hand, Olfr1393, 1392 and 90 are found on the cell surface only when co-expressed with RTP1S, Ric8b and $G_{\alpha olf}$ and one of the N-terminal tags (Lucy or Rho). Still, other ORs (i.e., Olfr691) properly traffic with either the Lucy tag or the accessory proteins (but not the Rho tag alone). Ideally, one would prefer to achieve surface expression with the minimal amount of modification to the OR protein itself. Importantly, as a classic signal peptide, the Lucy tag contains a putative cleavage site. As such, it is not present on the mature protein which reaches the plasma membrane (as demonstrated below, FIG. 10). Using the cleavable Lucy tag (in the absence of the 22-amino acid Rho tag), we are able to achieve surface expression of 10/15 ORs tested (Table 1, Column 6). This will allow for functional characterization of these ORs with only an 8-amino acid flag tag on the plasma membrane protein (previously, only 5 ORs reached the cell surface with a Flag tag alone, Table 1, Column 2).

Figure 14:
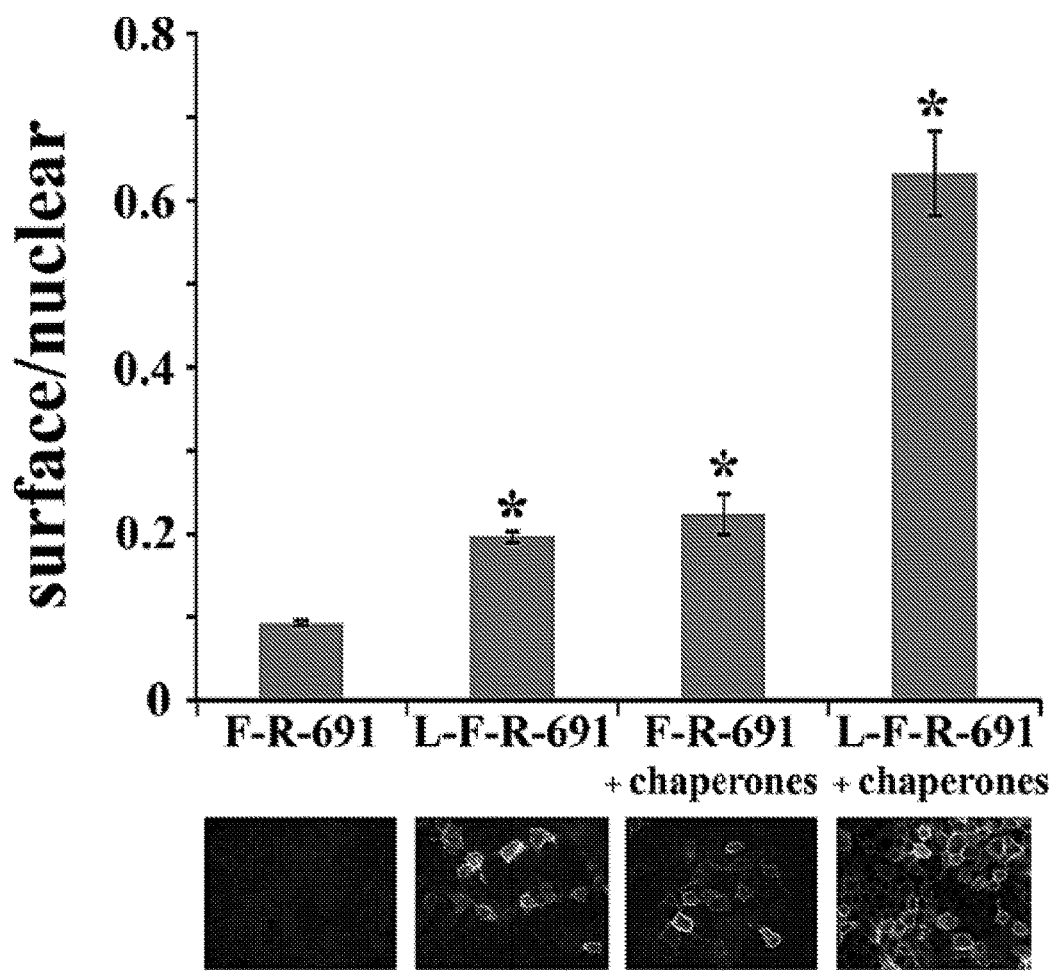
FIG. 14. The Lucy tag and accessory proteins increase the amount of Olfr691 detected on the cell surface. Surface-labeled Olfr691 was quantitated by measuring the mean fluorescence intensity for each image. This graph represents the mean fluorescence intensity normalized to the corresponding binary nuclear image for the same field of view (surface/nuclear). Error bars represent the SEM, and '+chaperones' indicates the presence of RTP1S, Ric8b and $G_{\alpha olf}$ Representative images corresponding to each condition are pictured below the graph showing the increased surface expression. For all conditions that promoted surface expression (Flag-Rho-691+chaperones, Lucy-Flag-Rho-691 and Lucy-Flag-Rho-691+chaperones), there was a significant increase in the surface/nuclear ratio as compared to Flag-Rho-691 (*P≤0.01 as measured by ANOVA and Student—Newman Keuls). In addition, the fluorescence for Lucy-Flag-Rho-691+chaperones was significantly increased as compared to both Lucy-Flag-Rho-691 and Flag-Rho-691+chaperones (P≤0.001).

Finally, although our goal was to achieve surface expression for ORs which did not previously reach the cell surface at all, we noted that some ORs appeared to have enhanced surface expression when both the Lucy tag and the accessory proteins were present (for example, Olfr78 and Olfr691 as seen in FIGS. 1 and 2). The increase in surface expression was confirmed when the fluorescent surface images were quantitated for Olfr691 (FIG. 14).

The Lucy Tag is Cleaved.

The Lucy tag is a putative cleavable signal peptide found on the N-terminus of LRRC32, and has been previously shown to be cleaved from the mature LRRC32 protein [28]. To determine whether the Lucy tag is also cleaved from the olfactory receptor constructs, we added an HA tag to the extreme N-terminus of both Rho-Olfr691 (FIG. 10A,B) and Lucy-Rho-Olfr691 (FIG. 10C,D). These constructs were then expressed in HEK293T cells along with RTP1S, which allows for Rho-tagged Olfr691 surface expression. The cells were stained in parallel with both an HA and Flag antibody to detect either the total OR population for both tags (FIG. 10A, C), or, on a separate coverslip, the cell surface membrane-associated receptor only for both tags (FIG. 10B, D). If the Lucy tag is cleaved, the HA tag should be removed (along with the Lucy tag) early on in the biosynthetic pathway and should not be detectable at the cell surface. When cells expressing HA-Flag-Rho-691 were stained, both Flag and HA antibodies could detect surface-associated (FIG. 10A) and intracellular receptor (FIG. 10B), indicating that both tags were present on the mature protein. However, when HA-Lucy-Flag-Rho-691 was surface labeled, the HA epitope was no longer present on the cell surface, although surface-associated receptor was still detectable via the Flag tag (FIG. 10D). In addition, while there was abundant intracellular Flag staining, there was only weak HA staining (FIG. 10C). Taken together, these results indicate that the Lucy tag acts as a functional, cleavable signal peptide when added to the N-terminus of ORs and is likely removed early on in the biosynthetic pathway.

The Lucy Tag Increases Total Protein Levels of all ORs.

Figure 11A:
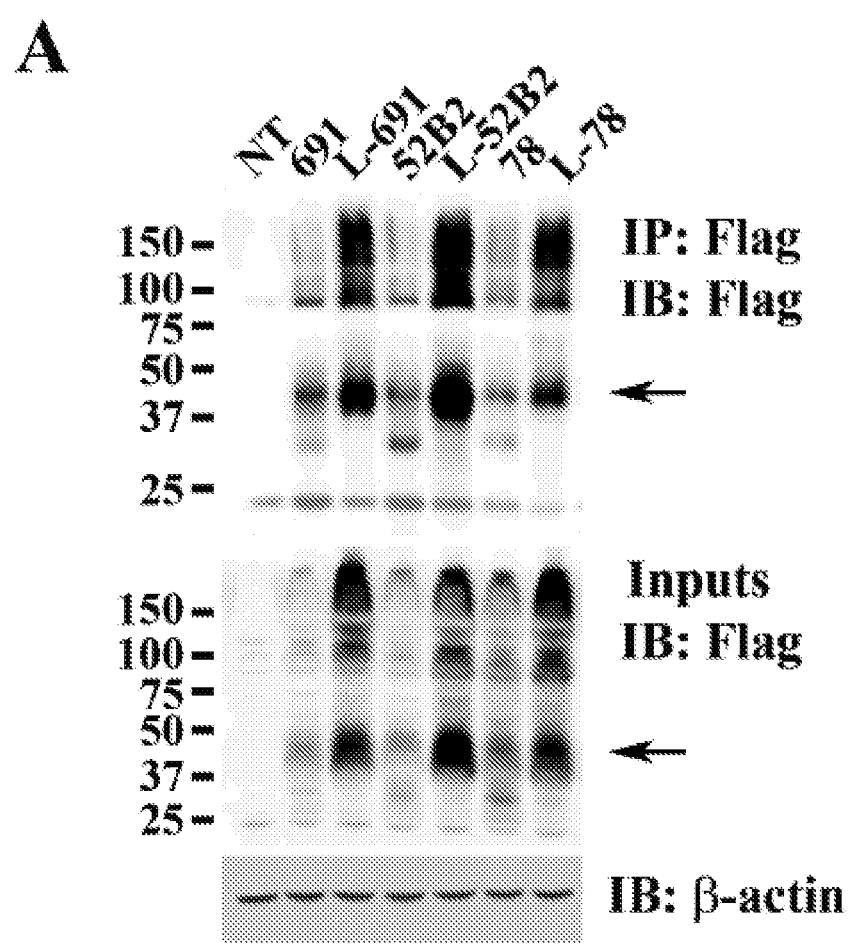
FIG. 11. The Lucy tag increases OR protein levels. (A) Rho-tagged and Lucy-Rho-tagged ORs (L-OR) were immunoprecipitated from HEK293T cells using monoclonal M2 Flag beads. Bound (B) lysates were immunoblotted with the Flag antibody to detect total OR levels. The arrow indicates the mature OR product at 39 kb. The input was also immunoblotted with the Flag antibody and then stripped and reprobed for β-actin to ensure equal loading. (B) An ELISA was performed for HEK293T cells expressing either Rho-tagged ORs or Lucy-Rho-tagged ORs to detect total OR levels using a monoclonal Flag antibody. Total protein levels are graphed as absorbance in arbitrary units. The dashed line indicates the background as measured by a non-transfected (NT) control. All measurements were performed in quadruplicate and the error bars indicate the SEM. An * represents significance as measured by the student T-test (Rho-OR vs. Lucy-OR) with P≤0.005 and a + represents significance with a P≤0.05. The Lucy tag increased total OR expression of ORs, as shown in both (A) and (B).
Figure 11B:
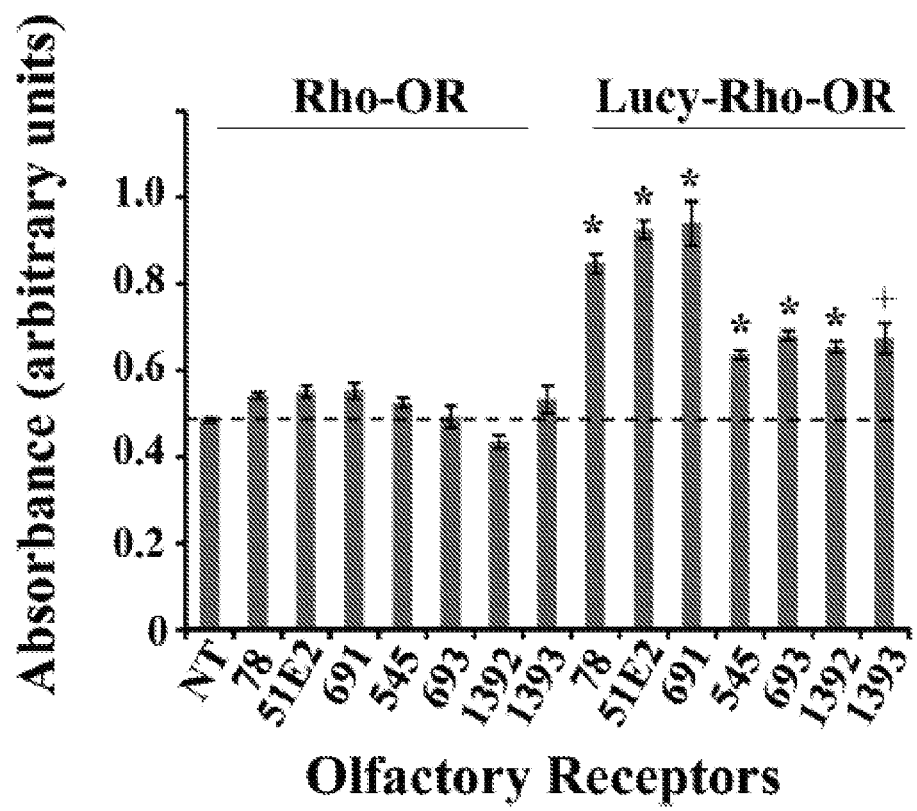

When staining HEK293T cells expressing either Rho-ORs or Lucy-Rho-ORs, we noted that there was consistently more surface and intracellular Flag staining with the Lucy tagged constructs (FIG. 13). Since Lucy is an ER signal peptide, it is possible that it stabilizes the protein, and thus, increases expression. To examine total protein levels, we transfected HEK293T cells with either Rho-OR or Lucy-Rho-OR constructs, lysed the cells, and immunoprecipitated the OR using M2 Flag beads. An aliquot of the original lysate (input) and the immunoprecipitated ORs were then immunoblotted with a Flag antibody and a subset of ORs are shown in FIG. 11A. Typically, ORs are detected as a complex of high-molecular weight bands, likely due to aggregation, degradation and other modifications [8,16], as seen in the whole cell extract (FIG. 11A input); immunoprecipitation (FIG. 11A IP: Flag) allows for improved resolution. Both the high molecular weight bands and a prominent band at 39 kDa (the predicted size of tagged ORs) were completely recovered in the bound lysate (no bands were detected in the unbound fraction). In both the immunoprecipitate and input lysate, the presence of the Lucy tag appears to increase total OR protein expression (FIG. 11A). To ensure equal loading, the immunoblot was stripped and reprobed for β-actin. To quantitate the increase in OR protein, we performed an ELISA to detect total Flag protein levels. As seen in FIG. 11B, levels of Rho-ORs were elevated just slightly above background (nontransfected control; dashed line). However, when the Lucy tag was added, protein levels of all ORs tested were increased (1.5-2 fold increase n=4, P≤0.005), suggesting that the Lucy tag may stabilize the expressed ORs (FIG. 11B).

Lucy does not Alter OR-Ligand Specificity.

OR surface expression in heterologous cell systems is a prerequisite for further functional studies, including OR deorphanization. Since Lucy is a cleaved signal peptide, it is not incorporated into the mature protein and thus, should not interfere with OR-ligand specificity or downstream signaling.

Figure 12A:
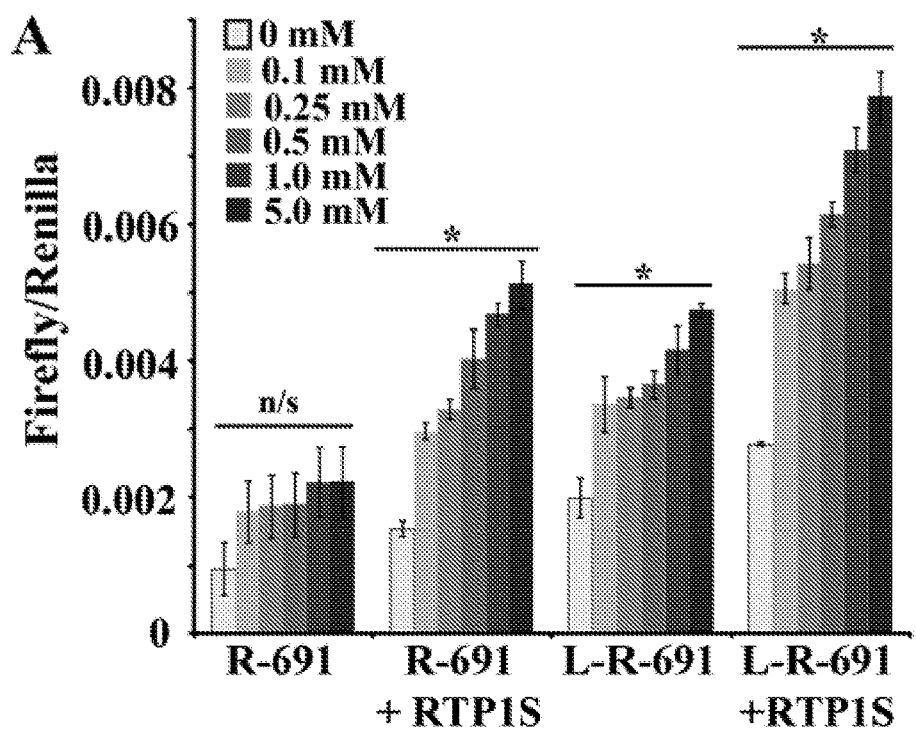
FIG. 12. The Lucy tag does not alter OR signaling. (A) A luciferase reporter assay was performed for both Rho-Olfr691(R-691) and Lucy-Rho-Olfr691 (L-R-691) with and without RTP1S. Cells expressing the Olfr691 constructs were grown in a 96-well plate and exposed to the known Olfr691 ligand, isovaleric acid (0-5 mM). Error bars represent the SEM. By ANOVA and Student-Newman-Keuls, no concentrations of isovaleric acid activated R-691 (n/s=no significance). For R-691+RTP1S, L-691, and L-691+RTP1S, P≤0.05 for 0 mM vs. all doses of isovaleric acid (marked by an *). In addition, for R-691+RTP1S, P≤0.05 for 5 vs. 0.5, 0.25 and 0.1, 1 vs. 0.25 and 0.1, 0.5 vs. 0.1. For L-691, P≤0.05 for 5 vs. 0.1, 0.25 and 0.5. For L-691+RTP1S, P≤0.05 for 5 vs. 0.5, 0.25 and 0.1, 1 vs. 0.5, 0.25 and 0.1, 0.5 vs. 0.1. (B) A luciferase reporter assay was performed for mOREG (EG), Rho-mOREG (R-EG), Lucy-mOREG (L-EG) and Lucy-Rho-mOREG (L-R-EG), all in the absence of RTP1S. Cells expressing the mOREG constructs were grown in a 96-well plate and exposed to the known mOREG ligand, eugenol (100-300 µM). Error bars represent the SEM. By ANOVA and Student-Newman-Keuls, all concentrations of eugenol significantly activated (P≤0.05) e.g., R-EG, L-EG and L-R-EG as compared to 0 µM (marked by an *). In addition, 100 and 300 µM eugenol were significant from each other (P≤0.05) for both L-EG and L-R-EG. In both A and B, the Firefly: Renilla ratio was measured and compared to the non-treated control. An increase in the ratio indicates OR activation. Both Lucy-Rho-691 and Lucy-tagged mOREG constructs were activated with their ligands indicating that the Lucy tag does not alter OR signaling.
Figure 15:
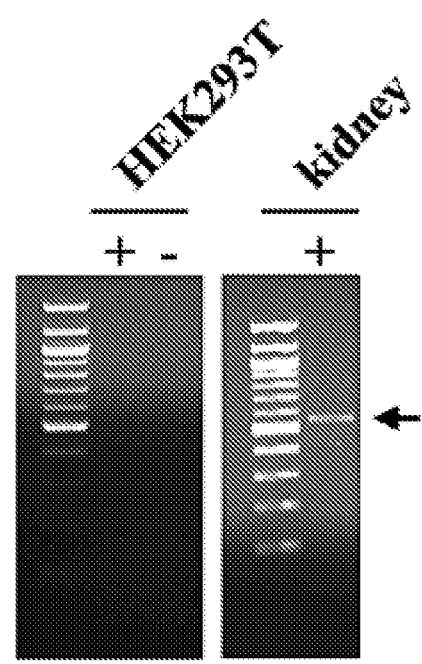
FIG. 15. HEK293T cells do not natively express RTP. HEK293T and whole kidney RNA was reverse transcribed with (+) or without (−) reverse transcriptase and PCR was performed using primers for both the long and short form of RTP. Amplified RTP had an expected size of 548 bp. RTP was amplified from kidney cDNA but not from HEK293T cDNA.

However, some data have suggested that ORs require a "co-receptor" (RTP1S) to signal properly [19]. To determine whether Lucy-tagged ORs expressed on the cell surface can still respond to their ligands in the absence of RTP1S, and to ensure that the Lucy tag is not altering ligand binding or detection, we assayed for a functional ligand response using a luciferase reporter assay [5]. In this assay, OR-ligand binding leads to an increase in cAMP which drives the expression of a CRE luciferase. An increase in the Firefly (CRE-dependent luciferase): Renilla (constitutively activated luciferase) ratio indicates OR activation. Previously, it was determined that Olfr691 responds to isovaleric acid [16]. Here, Rho-Olfr691 and Lucy-Rho-Olfr691 were expressed in HEK293T cells with or without RTP1S and exposed to 0.1-5 mM isovaleric acid. By itself, Rho-Olfr691 was not significantly activated at any concentration (FIG. 12A), confirming the lack of detectable surface expression as seen by immunofluorescence (FIG. 15). When Rho-Olfr691 was co-expressed with RTP1S, we observed a dose-dependent increase in the Firefly: Renilla ratio ($P \leq 0.002$ for all doses compared to 0 mM), confirming the previous findings (FIG. 12A). Lucy-Rho-Olfr691 also responded to isovaleric acid in a dose-dependent manner with and without the addition of RTP1S ($P \leq 0.007$ for all doses compared to 0 mM) confirming that the surface expression observed in FIGS. 1 and 2 represents functional protein. As seen in FIG. 12A, we found that OR constructs with higher surface expression (whether due to the Lucy tag, Rho tag, or chaperones) tended to have a higher Firefly/Renilla ratio at baseline (non-treated, NT) in the luciferase reporter assay. This often corresponded to a higher ratio with stimulation as well, implying that the increased baseline may indicate a low level of basal signaling in the absence of ligand.

To confirm that the Lucy tag does not interfere with OR-ligand binding and downstream signaling and that RTP1S is not required for proper activation, we also performed the luciferase reporter assay on mOREG (FIG. 12B). mOREG is a well-characterized OR known to respond to eugenol (hence its name). As mOREG is one of the ORs that reach the cell surface under every condition tested, we expressed the OR with and without the Lucy and Rho tags and assessed its response to eugenol. Every permeation of the mOREG construct resulted in a dose-dependent activation with eugenol ($P \leq 0.05$, 300 μM vs. 0 μM), once again suggesting that the cleavable Lucy tag does not interfere with OR-ligand binding and that properly trafficked ORs likely do not require a co-receptor for function.

Discussion

The limiting factor in OR deorphanization has been the ability—or, often, the inability—to heterologously express ORs on the cell surface. Here, we report that the addition of a leucine rich cleavable signal peptide (Lucy tag) onto the N-terminus of ORs significantly improves detectable surface expression, as well as total protein expression. When combined with RTP1S, Ric8b and $G_{\alpha olf}$ we found that all 15 of the Lucy-ORs that we examined successfully trafficked to the surface, providing promise for future deorphanization and other functional studies.

What is the mechanism of the Lucy tag? Cleavable signal peptides are natively found on secreted proteins and subsets of TMD proteins (including some GPCRs) [25,26]. Recognition of these cleavable peptides at the extreme N-terminus of the protein by the Signal Recognition Particle (SRP) promotes co-translational ER translocation and ensures that the complete mature protein is translated in the lumen of the ER (as opposed to the cytosol) [25,26]. When TMD proteins do not contain a cleavable signal peptide, one of the TMDs (usually the first) takes its place and acts as a signal anchor sequence. Therefore, a signal peptide at the N-terminus of proteins is not required for proper ER translocation and only 5-10% of GPCRs possess a classic signal peptide [26]. Typically, receptors that utilize a signal peptide have long N-terminal tails that can rapidly fold, preventing post-translational translocation across the ER membrane [26]. ORs do not have unusually long N-terminal tails, and it is possible that the co-translational ER entry via the Lucy tag helps to stabilize the receptor or prevents misfolding. In support of this, our preliminary studies showed that mRNA levels of Lucy and non-Lucy-tagged constructs were similar, despite the fact that total protein expression for all ORs was enhanced by the addition of the Lucy tag (FIG. 11). However, in addition to increasing total protein levels, the Lucy tag by itself promoted surface expression of some ORs (FIG. 15). This indicates that the Lucy tag has roles beyond protein translation and may be promoting some of the later steps of protein trafficking or ER exit. ORs do not natively possess signal peptides, but they are not retained in the ER when natively expressed in the olfactory epithelium (OE); thus, the Lucy tag must be helping ORs to overcome ER processing problems that are unique to heterologous expression. Although the Lucy tag does increase total expression, this increase does not appear to account for the increase in surface expression. In preliminary studies, we found that simply transfecting more of a Rho-tagged OR (in μg), did not correlate with increased surface expression. Therefore, the increase in both total and surface expression for Lucy-tagged ORs is unique to the tag itself.

It should be noted that the Lucy tag may be dependent on the immediate upstream sequence of the mature protein. Mutational studies have shown that signal peptides and their adjacent N-terminal sequences act as a "functional unit" and deletion of this upstream domain negatively affects ER translocation [26,35]. As our Lucy-tagged constructs contained a Flag tag (for detection purposes) following the cleavable peptide, the presence of this tag may be required for proper function and cleavage. Preliminary studies found that deletion of the Flag tag from a Lucy-Flag-OR construct prevented the OR from responding to its ligand, suggesting impaired surface expression (without the Flag tag, surface expression could not be assayed independently in this construct). It appears, then, that like other N-terminal sequences [26,35], the 'context' of the Lucy tag may be important for its function.

Multiple Blockage Steps for OR Trafficking.

Figure 12B:
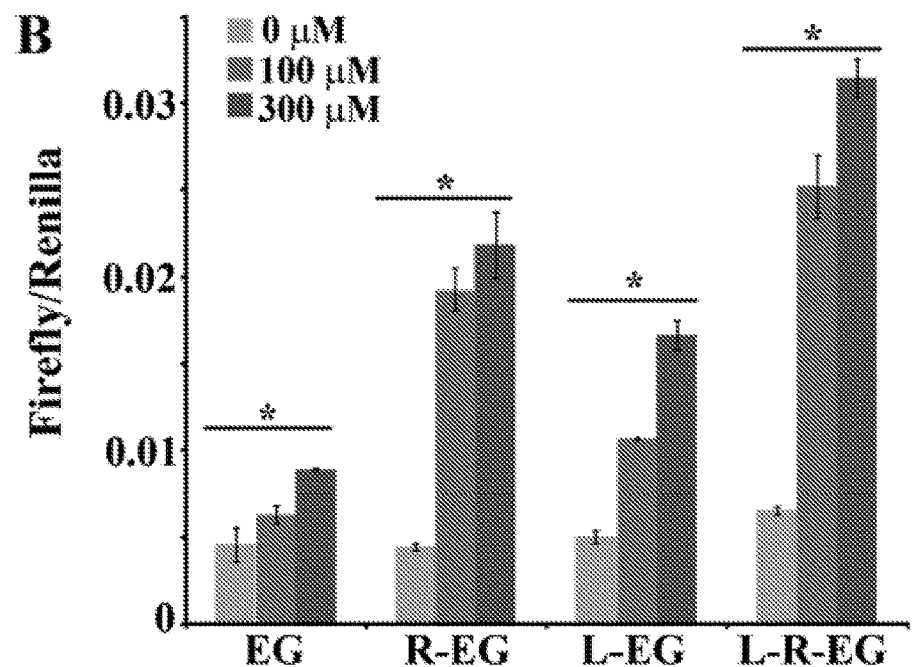

Studies have shown that ORs are retained in the ER when expressed in heterologous cells where they undergo ER-associated degradation [8,13,36,37]. However, as demonstrated by Wu, et al [19], the ER-Golgi transition step is not the only point of retention. This is evidenced in our work by the fact that, under the same conditions, some ORs are more efficiently trafficked to the cell surface than others, despite taking what is presumed to be a common route to the plasma membrane. For example, in this study Olfr78, hOR51E2 and mOREG trafficked to the cell surface even in the absence of the Rho tag. While the surface expression was relatively weak, mOREG does respond its ligand in the absence of the Rho tag (FIG. 12B). Others, however, required much more assistance to make it to the plasma membrane. Olfr545, Olfr985 and Olfr394 required both the Lucy and Rho tags as well as the co-transfection of RTP1S, Ric8b and $G_{\alpha olf}$ for proper surface expression. What can account for these differences? It is likely that some ORs are retained at multiple cellular checkpoints and each of these tags and accessory proteins function at one (or more than one) of these points. Further studies are clearly required to fully understand OR trafficking and the Lucy tag could prove to be a valuable tool to answer these questions.

What is the function of RTPIS?.

The current "gold standard" in OR trafficking was found to be the combination of a Rho tag with RTP1S, Ric8b and $G_{\alpha olf}$ [18]. Of these three accessory proteins, RTP1S is thought to be the most crucial as it can promote OR surface expression even in the absence of the other two compounds for some ORs [5, 15, 16, 22-24]. Indeed, we have found that RTP is often required for cell surface expression. By contrast, Gαolf is typically not required, and Ric8b is only occasionally necessary. RTP1S is natively expressed in the olfactory epithelium, and thus, it has been speculated that it is necessary for OR expression in both heterologous cells as well as the OE [16,18]. Recently, Wu et al performed a series of mutations and substitutions to RTP in order to elucidate the mechanism(s) of this important protein [19]. From this study, it was concluded that RTP1S and olfactory receptors (in this case Olfr599) interact throughout the biosynthetic pathway, and that individual domains of RTP1S are required for different stages of OR trafficking. It was also speculated that RTP1S may function as a co-receptor as the localization of both the OR and RTP to lipid raft domains was required for OR activation [19]. Indeed, much of our data is consistent with this study. Many of the ORs that we examined required RTP1S (with Ric8b and $G_{\alpha olf}$) for proper surface expression (i.e., Olfr693, Olfr1392, Olfr1393, Olfr90 and Olfr545). However, we also found that Olfr78, hOR51E2 and mOREG (FIG. 5B) were able to respond to their ligand even in the absence of RTP1S. To ensure that RTP is not natively expressed in HEK 293T cells, we performed RT-PCR using primers that could detect both the long and short form of RTP but did not detect any band in HEK293T cells (a positive control performed simultaneously gave a band of the expected size; Fig. S3). In addition, Olfr691 was functionally expressed on the cell surface (with the Lucy tag) in the absence of RTP1S, and retained a normal ligand response (FIG. 5A). While RTP is clearly playing important roles in the early trafficking steps and folding of olfactory receptors, it is not required for OR activation or surface expression and therefore is not an obligate co-receptor. Use of the Lucy tag can help shed new light on the functions of RTP1S, as OR function can now be assayed both with and without RTP (FIG. 12).

Potential for Deorphanization.

OR deorphanization has been greatly hampered by the inability to functionally express ORs in heterologous cell systems. To date, the addition of N-terminal tags or the co-expression of chaperone proteins has been crucial for surface expression of many receptors, but has not allowed for widespread OR deorphanization. In this study, we examined the trafficking of 15 diverse ORs with the Lucy tag, many of which are orphan receptors. Because the Lucy tag is cleaved prior to surface expression, this tag does not interfere with or alter ligand binding. In fact, for many ORs, the addition of the cleavable Lucy tag allowed surface expression even in the absence of the 22-amino acid Rho tag (FIGS. 1 and 2), allowing for the potential of OR deorphanization with only an 8 amino acid Flag tag on the mature protein. The identification of ligands for ORs is becoming increasingly important and has implications beyond olfaction. It has recently been demonstrated that ORs are expressed in multiple tissues outside of the OE [31, 38-43], where they play functional roles in processes as varied as muscle cell migration, renal function, and sperm chemotaxis. In order to understand the roles that ORs are playing both in the OE and in other tissues, ligand assignment is imperative. The addition of the Lucy tag represents a distinct improvement in the trafficking of heterologously expressed ORs which we hope will lead to future wide scale deorphanization studies.

REFERENCES

1. Godfrey P A, Malnic B, Buck L B (2004) The mouse olfactory receptor gene family. Proc Natl Acad Sci USA 101: 2156-2161.
2. Malnic B, Godfrey P A, Buck L B (2004) The human olfactory receptor gene family. Proc Natl Acad Sci USA 101: 2584-2589.
3. Buck L, Axel R (1991) A novel multigene family may encode odorant receptors: a molecular basis for odor recognition. Cell 65: 175-187.
4. Katada S, Nakagawa T, Kataoka H, Touhara K (2003) Odorant response assays for a heterologously expressed olfactory receptor. Biochem Biophys Res Commun 305: 964-969.
5. Zhuang H, Matsunami H (2008) Evaluating cell-surface expression and measuring activation of mammalian odorant receptors in heterologous cells. Nat Protoc 3: 1402-1413.
6. Touhara K (2007) Deorphanizing vertebrate olfactory receptors: recent advances in odorant-response assays. Neurochem Int 51: 132-139.
7. Wetzel C H, Oles M, Wellerdieck C, Kuczkowiak M, Gisselmann G et al. (1999) Specificity and sensitivity of a human olfactory receptor functionally expressed in human embryonic kidney 293 cells and Xenopus laevis oocytes. J Neurosci 19: 7426-7433.
8. Lu M, Echeverri F, Moyer B D (2003) Endoplasmic reticulum retention, degradation, and aggregation of olfactory G-protein coupled receptors. Traffic 4: 416-433.
9. McClintock T S, Sammeta N (2003) Trafficking prerogatives of olfactory receptors. Neuroreport 14: 1547-1552.
10. Mombaerts P (2004) Genes and ligands for odorant, vomeronasal and taste receptors. Nat Rev Neurosci 5: 263-278.
11. Gaillard I, Rouquier S, Pin J P, Mollard P, Richard S et al. (2002) A single olfactory receptor specifically binds a set of odorant molecules. Eur J Neurosci 15: 409-418.
12. Hague C, Uberti M A, Chen Z, Bush C F, Jones S V et al. (2004) Olfactory receptor surface expression is driven by association with the beta2-adrenergic receptor. Proc Natl Acad Sci USA 101: 13672-13676.
13. Lu M, Staszewski L, Echeverri F, Xu H, Moyer B D (2004) Endoplasmic reticulum degradation impedes olfactory G-protein coupled receptor functional expression. BMC Cell Biol 5: 34.
14. Hall R A (2009) Olfactory receptor interactions with other receptors. Ann. N Y Acad Sci 1170: 147-149.

15. Krautwurst D, Yau K W, Reed R R (1998) Identification of ligands for olfactory receptors by functional expression of a receptor library. Cell 95: 917-926.
16. Saito H, Kubota M, Roberts R W, Chi Q, Matsunami H (2004) RTP family members induce functional expression of mammalian odorant receptors. Cell 119: 679-691.
17. Matsunami H, Mainland J D, Dey S (2009) Trafficking of mammalian chemosensory receptors by receptor-transporting proteins. Ann N Y Acad Sci 1170: 153-156.
18. Zhuang H, Matsunami H (2007) Synergism of accessory factors in functional expression of mammalian odorant receptors. J Biol Chem 282: 15284-15293.
19. Wu L, Pan Y, Chen G Q, Matsunami H, Zhuang H (2012) Receptor-transporting protein 1 short (RTP1S) mediates translocation and activation of odorant receptors by acting through multiple steps. J Biol Chem 287: 22287-22294.
20. Von Dannecker L E, Mercadante A F, Malnic B (2006) Ric-8B promotes functional expression of odorant receptors. Proc Natl Acad Sci USA 103: 9310-9314.
21. Belluscio L, Gold G H, Nemes A, Axel R (1998) Mice deficient in G(olf) are anosmic. Neuron 20: 69-81.
22. Kajiya K, Inaki K, Tanaka M, Haga T, Kataoka H et al. (2001) Molecular bases of odor discrimination: Reconstitution of olfactory receptors that recognize overlapping sets of odorants. J Neurosci 21: 6018-6025.
23. Nara K, Saraiva L R, Ye X, Buck L B (2011) A large-scale analysis of odor coding in the olfactory epithelium. J Neurosci 31: 9179-9191.
24. Saito H, Chi Q, Zhuang H, Matsunami H, Mainland J D (2009) Odor coding by a Mammalian receptor repertoire. Sci Signal 2: ra9.
25. Zimmermann R, Eyrisch S, Ahmad M, Helms V (2011) Protein translocation across the E R membrane. Biochim Biophys Acta 1808: 912-924.
26. Schulein R, Westendorf C, Krause G, Rosenthal W (2012) Functional significance of cleavable signal peptides of G protein-coupled receptors. Eur J Cell Biol 91: 294-299.
27. Zampatis D E, Rutz C, Furkert J, Schmidt A, Wustenhagen D et al. (2012) The protease-activated receptor 1 possesses a functional and cleavable signal peptide which is necessary for receptor expression. FEBS Lett 586: 2351-2359.
28. Chan D V, Somani A K, Young A B, Massari J V, Ohtola J et al. (2011) Signal peptide cleavage is essential for surface expression of a regulatory T cell surface protein, leucine rich repeat containing 32 (LRRC32). BMC Biochem 12: 27: 1471-2091
29. Dunham J H, Hall R A (2009) Enhancement of the surface expression of G protein-coupled receptors. Trends Biotechnol 27: 541-545.
30. Guan X M, Kobilka T S, Kobilka B K (1992) Enhancement of membrane insertion and function in a type Mb membrane protein following introduction of a cleavable signal peptide. J Biol Chem 267: 21995-21998.
31. Pluznick J L, Zou D J, Zhang X, Yan Q, Rodriguez-Gil D J et al. (2009) Functional expression of the olfactory signaling system in the kidney. Proc Natl Acad Sci USA 106: 2059-2064.
32. Bryksin A V, Matsumura I (2010) Overlap extension PCR cloning: a simple and reliable way to create recombinant plasmids. BioTechniques 48: 463-465.
33. Hansson M D, Rzeznicka K, Rosenback M, Hansson M, Sirijovski N (2008) PCR-mediated deletion of plasmid DNA. Anal Biochem 375: 373-375.
34. Chapin H C, Rajendran V, Capasso A, Caplan M J (2009) Detecting the surface localization and cytoplasmic cleavage of membrane-bound proteins. Methods Cell Biol 94: 223-239.
35. Bush C F, Hall R A (2008) Olfactory receptor trafficking to the plasma membrane. Cell Mol Life Sci 65: 2289-2295.
36. Alken M, Schmidt A, Rutz C, Furkert J, Kleinau G et al. (2009) The sequence after the signal peptide of the G protein-coupled endothelin B receptor is required for efficient translocon gating at the endoplasmic reticulum membrane. Mol Pharmacol 75: 801-811.
37. Jacquier V, Prummer M, Segura J M, Pick H, Vogel H (2006) Visualizing odorant receptor trafficking in living cells down to the single-molecule level. Proc Natl Acad Sci USA 103: 14325-14330.
38. Griffin C A, Kafadar K A, Pavlath G K (2009) MOR23 promotes muscle regeneration and regulates cell adhesion and migration. Dev Cell 17: 649-661.
39. Pavlath G K (2010) A new function for odorant receptors: MOR23 is necessary for normal tissue repair in skeletal muscle. Cell Adh Migr 4: 502-506.
40. Spehr M, Gisselmann G, Poplawski A, Riffell J A, Wetzel C H et al. (2003) Identification of a testicular odorant receptor mediating human sperm chemotaxis. Science 299: 2054-2058.
41. Spehr M, Schwane K, Riffell J A, Zimmer R K, Hatt H (2006) Odorant receptors and olfactory-like signaling mechanisms in mammalian sperm. Mol Cell Endocrinol 250: 128-136.
42. Zhang X, Rogers M, Tian H, Zhang X, Zou D J et al. (2004) High-throughput microarray detection of olfactory receptor gene expression in the mouse. Proc Natl Acad Sci USA 101: 14168-14173.
43. Zhang X, De la Cruz O, Pinto J M, Nicolae D, Firestein S et al. (2007) Characterizing the expression of the human olfactory receptor gene family using a novel DNA microarray. Genome Biol 8: R86.

We claim:

1. An isolated nucleic acid comprising the nucleotide sequence set forth in SEQ ID NO: 1.

2. An isolated nucleic acid comprising a nucleotide sequence encoding the amino acid sequence of SEQ ID NO:2.

3. A protein comprising the amino acid sequence set forth in SEQ ID NO:2.

4. A system for increasing surface expression of proteins comprising:
   a. a vector comprising the nucleotide sequence of claim 2; and
   b. a vector encoding a chaperone protein that aids in expression, signaling and/or trafficking of the protein to the cell surface.

5. The system of claim 4, wherein the protein is an olfactory receptor.

6. The system of claim 4, wherein the chaperone protein is a receptor trafficking protein.

7. The system of claim 6, wherein the receptor trafficking protein is selected from the group consisting of RTPL1, RTP1S, and RTP2.

8. The system of claim 4, wherein the chaperone protein is Receptor Expressing Enhancing Protein (REEP).

9. The system of claim 4, wherein the chaperone protein is β-adrenergic receptor.

10. The system of claim 4, wherein the chaperone protein is heat shock protein 70 homolog.

11. The system of claim 4, wherein the chaperone protein is Resistance to Inhibitors of Cholinesterase 8 homolog B (Ric8b).

12. The system of claim 4, wherein the chaperone protein is Olfactory G-protein (Gαolf).

13. The system of claim 4, further comprising a cell line.

14. A system for increasing surface expression of proteins comprising:
   a. a vector comprising a nucleotide sequence encoding SEQ ID NO:3, wherein the nucleotide sequence is operably linked to a nucleotide sequence encoding a heterologous protein of interest; and
   b. one or more of a vector encoding RTP1S, a vector encoding Ric8b, and/or a vector encoding Gαolf.

15. The system of claim 14, wherein the nucleotide sequence encoding SEQ ID NO:3 further comprises a nucleotide sequence encoding an HA tag.

16. The system of claim 14, wherein the nucleotide sequence encoding SEQ ID NO:3 further comprises a nucleotide sequence encoding Rho tag.

17. The system of claim 15, wherein the nucleotide sequence encoding SEQ ID NO:3 further comprises a nucleotide sequence encoding Rho tag.

18. The system of claim 17, wherein the nucleotide sequence encoding SEQ ID NO:3 further comprises a linker between the HA tag and the Rho tag.

19. A system for increasing surface expression of proteins comprising:
   a. a vector comprising a nucleotide sequence encoding SEQ ID NO:2; and
   b. one or more of a vector encoding RTP1S, a vector encoding Ric8b, and/or a vector encoding Gαolf.

20. A system for increasing surface expression of olfactory receptors comprising:
   a. a vector comprising a nucleotide sequence encoding SEQ ID NO:2; and
   b. one or more of a vector encoding RTP1S, a vector encoding Ric8b, and/or a vector encoding Gαolf.

21. A system for increasing surface expression of proteins comprising:
   a. a vector comprising a nucleotide sequence encoding SEQ ID NO:3, wherein the nucleotide sequence is operably linked to a nucleotide sequence encoding a heterologous protein of interest; and
   b. a vector encoding a chaperone protein that aids in expression, signaling and/or trafficking of the protein to the cell surface.

* * * * *